United States Patent [19]
Christensen et al.

[11] 4,269,873
[45] * May 26, 1981

[54] 2-, 5-, AND 6-SUBSTITUTED-1-CARBADETHIAPEN-2-EM-3-CARBOXYLIC ACIDS

[75] Inventors: Burton G. Christensen, Scotch Plains; David B. R. Johnston, Warren; Susan M. Schmitt, Scotch Plains, all of N.J.

[73] Assignee: Merck & Co., Inc., Rahway, N.J.

[*] Notice: The portion of the term of this patent subsequent to Apr. 28, 1998, has been disclaimed.

[21] Appl. No.: 60,552

[22] Filed: Jul. 25, 1979

[51] Int. Cl.³ ............... C07D 487/04; A61K 31/40
[52] U.S. Cl. .................. 424/274; 260/239 A; 260/245.2 T; 424/248.52; 424/250; 424/263; 424/267; 542/413; 542/416; 546/157; 546/200; 546/272; 544/90; 544/132; 544/144; 544/298
[58] Field of Search ............... 260/245.2 T; 424/274, 424/248.52, 263; 546/272, 200; 544/298, 144, 132

[56] References Cited
U.S. PATENT DOCUMENTS

| | | | |
|---|---|---|---|
| 4,153,714 | 5/1979 | Donsford | 260/245.2 T |
| 4,181,733 | 1/1980 | Christensen et al. | 260/245.2 T |

OTHER PUBLICATIONS

Derwent Abs. 33719B, (Eur. Patent App. 1628), (5/2/79).
Johnston et al., Heterocycles, vol. 9, No. 6, p. 791, (1978).

*Primary Examiner*—Mary C. Lee
*Attorney, Agent, or Firm*—Frank M. Mahon; James A. Arno; Hesna J. Pfeiffer

[57] ABSTRACT

Disclosed are 2-, 5- and 6-substituted-1-carbadethiapen-2-em-3-carboxylic acids having the structure:

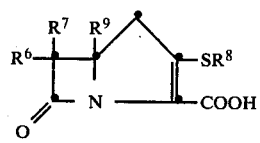

I wherein $R^6$, $R^7$, $R^8$ and $R^9$ are, inter alia, independently selected from the group consisting of hydrogen, ($R^9$ is not hydrogen), alkyl, alkenyl, aryl and aralkyl. Such compounds, as well as their pharmaceutically acceptable salt, ester and amide derivatives, are useful as antibiotics. Also disclosed are processes for the preparation of such compounds and methods of treatment comprising administering such compounds and compositions when an antibiotic effect is indicated.

7 Claims, No Drawings

2-, 5-, AND 6-SUBSTITUTED-1-CARBADETHIAPEN-2-EM-3-CARBOXYLIC ACIDS

BACKGROUND OF THE INVENTION

This invention relates to 2-,5- and 6-substituted-1-carbadethiapen-2-em-3-carboxylic acids (I) and the pharmaceutically acceptable salt, ester and amide derivatives thereof which are useful as antibiotics:

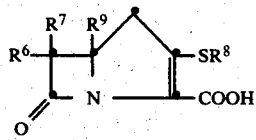

wherein $R^6$, $R^7$, $R^8$ and $R^9$ are independently selected from the group consisting of hydrogen, ($R^9$ is not hydrogen) substituted and unsubstituted: alkyl, alkenyl, and alkynyl, having from 1-10 carbon atoms, cycloalkyl, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the alkyl chain has 1-6 carbon atoms; heteroaryl, heteroaralkyl, heterocyclyl and heterocyclylalkyl wherein the substituent or substituents relative to the above-named radicals are selected from the group consisting of: amino, mono-, di- and trialkylamino, hydroxyl, alkoxyl, mercapto, oximino, alkylthio, arylthio such as phenylthio, sulfamoyl, ureido, amidino, guanidino, nitro, chloro, bromo, fluoro, cyano and carboxy; and wherein the hetero atom or atoms in the above-named heterocyclic moieties are selected from the group consisting of 1-4 oxygen, nitrogen or sulphur atoms; and wherein the alkyl moieties of the above-recited substituents have 1-6 carbon atoms.

This invention also relates to the carboxyl derivatives of I which are antibiotics and which may be represented by the following generic structure (I):

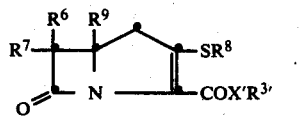

wherein $X'$ is oxygen, sulphur or $NR'$ ($R'=H$ or lower alkyl having 1-6 carbon atoms); and $R^{3'}$ is, inter alia, representatively selected from the group consisting of hydrogen, conventional blocking groups such as trialkylsilyl, acyl and the pharmaceutically acceptable salt, ester and amide moieties known in the bicyclic β-lactam antibiotic art; the definition of $R^{3'}$ is given in greater detail below.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes,* and *B. subtilis,* and gram negative bacteria such as *E. coli,* Pseudomonas, *Proteus morganii,* Serratia, and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

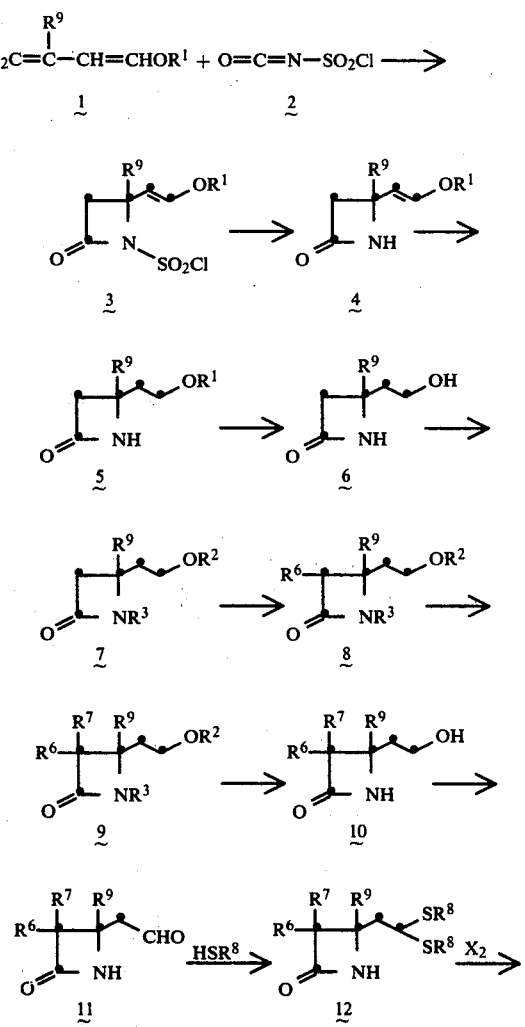

-continued

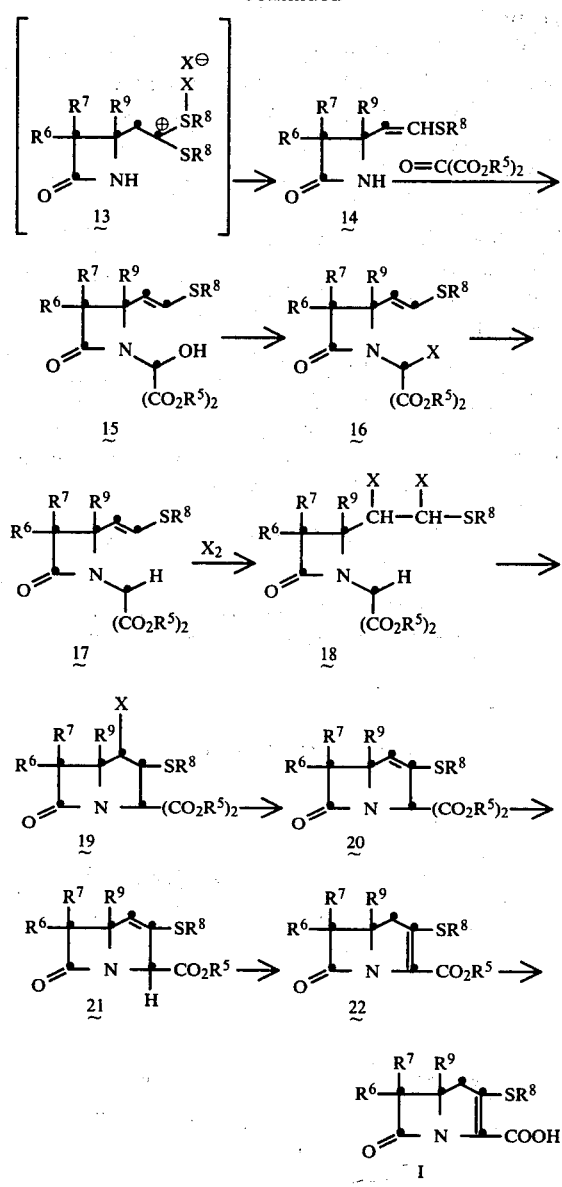

In words relative to the above diagram, the 4-substituted-4-(2-substituted-vinyl)azetidine-2-one, 4, starting material is prepared by reacting a 1-R¹-oxy-3-substituted-butadiene, 1, with chlorosulfonylisocyanate 2. The reaction is conducted without solvent or may be run in solvent such as diethyl ether, ethyl acetate, chloroform, methylene chloride, or the like, at a temperature of from −78° C. to 25° C. for from a few minutes to 1 hour to provide 3. The radical R¹ is an easily removable acyl blocking group such as alkanoyl or aralkanoyl which bears no functional group or groups which might interfere with the desired course of reaction (1+2→3→4). Intermediate species 3 is converted by reduction to the sulfinamide which is then hydrolyzed to 4 at pH 6–8. Typically the reaction solution comprising 3 is contacted (5–30 minutes) with an aqueous solution (at 0°–25° C.) of a reducing agent such as sodium sulfite, thiophenol, or the like, at pH 6–8 to provide 4.

The reaction 4→5 is a reduction, and is preferably achieved by hydrogenation in a solvent such as ethyl acetate, ether, dioxane, tetrahydrofuran (THF), ethanol or the like at 0° to 25° C. for from 5 minutes to 2 hours under 1 to 10 atmospheres of hydrogen in the presence of a hydrogenation catalyst such as a platinum metal or oxide thereof such as 10% Pd/C or the like.

The de-blocking reaction 5→6 is usually desirable when R¹ is acyl to permit the later alkylation, 7→8. The preferred de-blocking procedure is by alcoholysis wherein the solvent is a lower alkanol such as methanol, ethanol or the like in the presence of the corresponding alkali metal alkoxide, such as sodium methoxide. Typically, the reaction is conducted for from 5 minutes to 1 hour at a temperature of from −10° to 25° C.

Blocking groups R³ and R² are established (6→7) to provide a suitably protected species for alkylation (7→8→9). There is no criticality in the choice of blocking groups, provided only that they do not interfere with the intended alkylation. R³ may be hydrogen, a triorganosilyl group such as trimethylsilyl or the like, or a cyclic ether such as 2-tetrahydropyranyl. R² may also be a cyclic ether such as 2-tetrahydropyranyl; alternatively R³ and R² may be joined together to form protected species such as 7a:

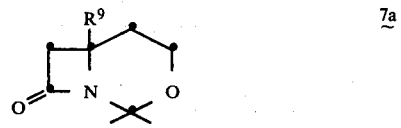

For example, species such as 7a are conveniently prepared by treating 6 with 2,2-dimethoxypropane in the presence of a catalyst such as boron trifluoride etherate, toluene sulphonic acid, or the like in a solvent such as methylene chloride, ether, chloroform, dioxane or the like at a temperature of from −10° C. to 35° C. for from a few minutes to 1 hour. Species 7 can be mono- or dialkylated at ring position 6. Alkylation of 7 provides 8. Typically, 7 is treated with a strong base such as lithium diisopropyl amide, sodium hydride, phenyl lithium or butyl lithium and the like in a solvent such as tetrahydrofuran (THF), ether, dimethoxyethane and the like at a temperature of from −80° C. to 0° C., whereupon the alkylating agent of choice, R⁶X, is added (R⁶ is as described above and X is chloro, iodo or bromo; alternatively the alkylating agent may be R⁶-tosylate, R⁶-mesylate or an aldehyde or ketone such as acetaldehyde and the like) to provide monoalkylated species 8. When desired, dialkylated species 9 may be obtained from 8 by repeating the alkylating procedure, 7→8.

The de-blocking reaction 9→10 is typically conducted by acid hydrolysis such as aqueous acetic acid at a temperature of from 25° C. to 75° C. for from 5 minutes to 3 hours.

The aldehyde intermediate 11 is prepared by treating 10 with an oxidizing agent such as CrO₃.2 (pyridine) in CH₃CN, 1:1 mixture of dimethylsulfoxide and acetic anhydride, cyclohexylcarbodiimide in DMSO or the like at a temperature of from 0°–25° C. for from 5 minutes to 1 hour. The resulting species 11 in a solvent such as acetonitrile, methylene chloride, chloroform or the like at a temperature of from −10° to 25° C. is treated with an excess of the reagent HSR⁸ in the presence of an acid catalyst such as boron trifluoride etherate, toluene sulphonic acid or the like to provide 12. Typically, the reaction requires from 1 to 60 minutes.

The vinyl sulphide 14 is obtained via intermediate 13 by treating 12 with a halogen such as chlorine or bromine (X=Cl or Br) in a solvent such as ether, methylene chloride, tetrahydrofuran, glyme or the like at a temperature of from −78° to 30° C. for from 1 to 30 minutes, followed immediately by treating with an olefin such as cyclohexene, isobutylene, or the like in the presence of base such as triethylamine, DBU, sodium hydride, or the like in a solvent such as DMF, glyme, THF, HMPA. The solution is held at −20° to 25° C. for from 1 to 8 hours to yield 14.

The vinyl sulphide species 14 is reacted with a diester of oxomalonic acid (or its monohydrate) to provide 15. There is no criticality as to the identity of the ester moiety, $R^5$, of the oxomalonic acid. $R^5$ may be a conventional, easily removable blocking group or it may be a pharmaceutically acceptable ester moiety. Suitable ester radicals $R^5$ are p-nitrobenzyl, benzyl, o-nitrobenzyl, t-butyl, 2,2,2-trichloroethyl. The reaction 14→15 is typically conducted in a high boiling organic solvent such as benzene, toluene, cyclohexane, halo aromatic or the like at a temperature of from about 50° C. to reflux for from 0.5 to 6 hours.

The halogenation reaction 15→16 is typically conducted in a solvent such as THF, glyme, ether, methylene chloride, chloroform or the like in the presence of a halogenating agent such as thionyl chloride, phosphorous pentachloride or the like in the presence of base such as pyridine at a temperature of from −20° to 25° C. for from 5 minutes to 3 hours. The selective reduction of 15→17 via 16 is completed by treating 16 with tributylphosphine, triphenylphosphine or the like in aqueous DMF or similar aqueous systems involving dioxane, THF, glyme, DMSO, or acetone in the presence of $K_2HPO_4$ at a temperature of from about 0°–50° C. for from 10 minutes to 5 hours.

Species 17 is halogenated by the previous procedure (12→13), but omitting the addition of the cyclohexene or other olefin, to provide the dihalo species 18. Species 18 is treated with a base such as triethylamine, sodium hydride or potassium hydride in a solvent such as DMF, acetonitrile, methylene chloride, chloroform, glyme or the like at a temperature of from about −78° to 25° C. for 1 to 5 hours to provide 19. Species 19 is converted to 20 on treatment with a strong base such as 1,5-diazabicyclo [5.4.0]-undec-5-ene(DBU),1,5-diazabicyclo[3.4.0]non-5-ene(DBN), or the like in a solvent as DMSO, acetone, chloroform, DMF, THF, glyme or the like or on treatment with AgF in pyridine at a temperature of from 0°–40° C. for from ¼ to 24 hours. The reaction 20→21 is conducted by treating 20 with an aromatic base such as pyridine, aqueous dimethylsulfoxide, s-collidine or lutidine, in the presence of a displacing agent such as lithium iodide, sodium chloride, lithium bromide, sodium bromide, or the like at a temperature of from about 80°–150° C. for from 15 minutes to 2 hours. An aqueous work up of the resulting reaction mixture provides 21. Isomerization of the double bond 21→22 is accomplished by treating 21 in a solvent such as DMF, DMSO, ethyl ether, THF, glyme, methylene chloride with a strong base such as diisopropylamine, DBU, DBN, or the like at a temperature of from 0° to about 25° C. for from a few minutes to 2 hours or until equilibrium has been established as determined by examination of sample aliquots by ultraviolet absorption or by thin layer chromatography. The final reaction 22→I (hydrogenolysis of the blocking group or groups) is accomplished by treating 22 in a solvent such as dioxane, ethanol, THF or the like or an aqueous mixture thereof in the presence of a Platinum metal catalyst such as Pd/C under a hydrogen pressure of from 1–4 atmospheres for from 0.5 to 8 hours at a temperature of from about 0°–25° C.

The above-described total synthesis may also advantageously start with a 4-substituted 4-vinyl azetidinone (23, below), rather than the enol acylate azetidinone (4, above). The following scheme illustrates this 4-vinyl azetidinone embodiment of the present invention; notice that it ties into the above scheme at species 14.

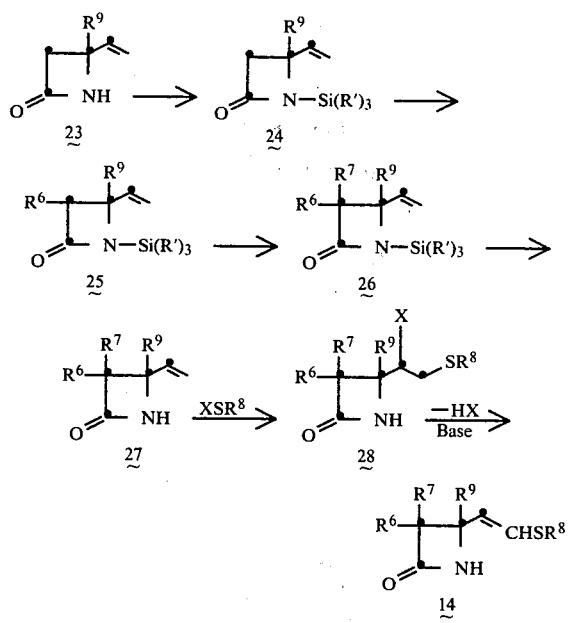

In words relative to the above reaction diagram, a 4-substituted 4-vinyl azetidinone 23 is silylated to provide the N-silyl species 24. The groups R' on the silyl radical are lower alkyl having from 1–6 carbon atoms especially preferred triorganosilyl groups are trimethylsilyl and t-butyl-dimethylsilyl. Typically, the silylation (23→24) is achieved by treating 23 in a solvent such as DMF, DMSO, HMPA or the like with the silylating agent of choice, dimethyl t-butylsilyl chloride, and a base such as $Et_3N$, pyridine, N,N-dimethylaniline and the like at a temperature of from −10° to 30° C. for from 1 to 8 hours. Species 24 is alkylated to form 25 or 26 and this alkylation is conducted exactly as described above for the alkylation 7→8→9. The removal of the N-triorganosilyl group is accomplished in reaction 26→27 by mild acid catalyzed solvolysis. The halo sulfide species 28 is obtained from 27 by treating 27 in a solvent such as methylene chloride, THF, glyme, or the like with the reagent $XSR^8$ wherein $R^8$ has previously been defined and X is halogen such as chloro or bromo at a temperature of from −50° to 50° C. for from 1 to 16 hours. The vinyl sulfide intermediate 14, which is common to the above illustrated scheme of total synthesis is obtained from 28 by elimination of HX on treatment of 28 with a base such as 1,5-diazabicyclo[5.4.0]undec-5-ene (DBU), 1,5-diazabicyclo[4.3.0]non-5-ene, (DBN), 1,4-diazabicyclo[2.2.2]octane, (DABCO), or silver fluoride in a solvent such as DMSO, pyridine, DMF, HMPA or the like at a temperature of from −20° to 50° C. for from ¼ to 16 hours.

In the foregoing description of the invention, suitable reagents HSR$^8$ (11→12) and XSR$^8$ (27→28) are representatively illustrated by the following list:

HSCH$_2$CH$_2$CH$_2$NHCO$_2$PNB,

PNBO$_2$CNHCH$_2$CH$_2$CH$_2$SX,

HSCH$_2$—⟨⟩—NO$_2$,

XSCH$_2$—⟨⟩—NO$_2$,

HSC(CH$_3$)$_2$CH$_2$NHCO$_2$PNB,

XSC(CH$_3$)$_2$CH$_2$NHCO$_2$PNB,

HSφ,

XSφ,

HSCH$_2$φ,

XSCH$_2$φ,

HSC(CH$_3$)$_3$,

XSC(CH$_3$)$_3$,

HSCφ$_3$,

XSCφ$_3$, $$CH_3 \underset{S}{\overset{N-N}{\diagdown\diagup}} SH$$

$$CH_3 \underset{S}{\overset{N-N}{\diagdown\diagup}} SX,$$

and the like (φ=phenyl; PBN=p-nitrobenzyl and X=chloro or bromo).

CH$_3$SH,

CH$_3$CH$_2$SH,

CH$_3$(CH$_2$)$_2$SH (CH$_3$)$_2$CHSH,

CH$_3$(CH$_2$)$_3$SH, (CH$_3$)$_2$CH(CH$_2$)$_2$SH,

⟨⟩—SH

φ(CH$_2$)$_3$SH (φ = PHENYL),

φ(CH$_2$)$_2$SH,

PNBO$_2$C(CH$_2$)$_2$SH

PNBO$_2$CNH(CH$_2$)$_2$SH

-continued

CH$_3$(CH$_2$)$_2$N(CO$_2$PNB)—(CH$_2$)$_2$SH

⟨⟩—N(CO$_2$PNB)(CH$_2$)$_2$SH (CH$_3$)$_2$N(CH$_2$)$_2$SH, (CH$_3$CH$_2$)$_2$N(CH$_2$)$_2$SH,

RO$_2$C(CH$_2$)$_2$SH, (R = benzyl)

φCH$_2$SH, (X)$_n$—⟨⟩—SH (n = 0, 1 or 2; X = Cl, Br, F, Cl, OCH$_3$, CH$_3$NH$_2$, NH$\overset{O}{\overset{\|}{C}}$CH$_3$), $$CH_3 \underset{S}{\overset{N-N}{\diagdown\diagup}} SH$$

$$HS \underset{\underset{CH_3}{N}}{\overset{N\diagdown N}{\diagdown\diagup}}$$

Y—⟨⟩$\underset{X}{\overset{N}{\diagdown\diagup}}$—SH (when X = N, O, S, Y = H; when X = S, Y = H, OCH$_2$CH$_3$, Cl)

⟨N⟩—SH

⟨N⟩—SH

⟨⟩⟨N⟩—SH

⟨$\underset{S}{N}$⟩—SH

⟨O⟩—SH

RN⟨$\overset{N}{\underset{N}{\diagdown\diagup}}$⟩—SH (R = p-nitroCbz = p-nitrobenzyloxycarbonyl)

Similarly, suitable alkylating agents for establishing R$^6$ and/or R$^7$ at ring position 6 (7→8→9) are:

φCH$_2$CHO,

φCH$_2$CH$_2$CHO,

-continued

CH₂O,

CH₃I,

φCH₂Br,

CH₃COCH₃,

CH₃CH(CH₃)CHO,

CH₃(CH₃)CHCH₂CHO,

CH₃CH₂CHO,

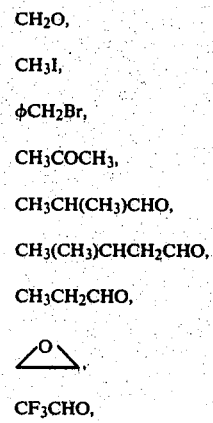

CF₃CHO,

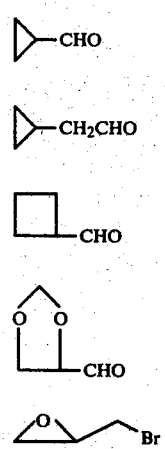

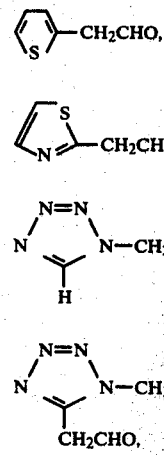

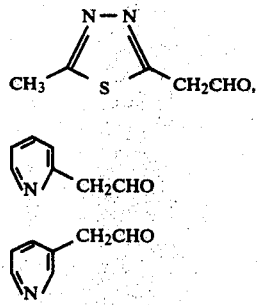

-continued

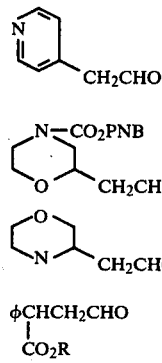

φCHCH₂CHO
|
CO₂R

R is removable carboxyl protecting group, such as benzyl.

A particularly preferred class of compounds when the 2-substituent (—SR⁸) of Structure I is amino-substituted alkylthio (e.g., —SCH₂CH₂NH₂, for example) is those prepared according to the teachings of Belgian Pat. No. 848,545 which patent describes the derivatization of the amino group to obtain, inter alia, amidines and guanidines. The patent is incorporated herein by reference.

Embodiments of Structure I, above, wherein R⁹ is hydrogen

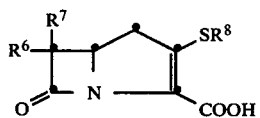

are disclosed and claimed in co-pending, commonly assigned U.S. Patent Applications Ser. Nos. 933,681 and 31,694, both now abandoned. These applications are incorporated herein by reference, since the instantly described total synthesis is by analogy to the incorporated applications. The instant process differs only in the R⁹-substituted acyloxybutadiene starting material.

Relative to the above-given generic description of the present invention (I):

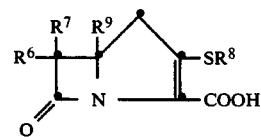

preferred values for R⁹ are: substituted and unsubstituted: alkyl having 1-6 carbon atoms, phenyl, phenylalkyl having 7-12 carbon atoms, CF₃, cycloalkyl having 3-6 carbon atoms, cycloalkylalkyl having 3-6 ring carbon atoms and 1-6 carbon atoms in the alkyl moiety, and heteroaryl having 4-6 ring atoms, one or more of which is O, N or S, wherein the substituent or substituents on the foregoing radicals are selected from: COOH, OH, NH₂, Cl, F, Br, alkyl and alkoxy having 1-3 carbon atoms.

A noted above, the compounds of the present invention may also generally be represented by the following structural formula:

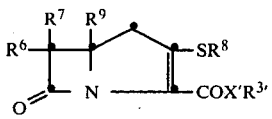

wherein X' is oxygen, sulfur or NR' (R' is hydrogen or loweralkyl having from 1 to 6 carbon atoms); and R³' is hydrogen, or, inter alia, is representatively selected to provide the pharmaceutically acceptable salt, ester, anhydride (R³' is acyl) and amide moieties known in the bicyclic β-lactam antibiotic art.

IDENTIFICATION OF THE RADICAL -COX'R³'

In the generic representation of the compounds of the present invention (I, above), the radical represented by —COX'R³' is, inter alia, —COOH (X' is oxygen and R³' is hydrogen) and all radicals known to be effective as pharmaceutically acceptable ester, anhydride (R³' is acyl) and amide radicals in the bicyclic β-lactam antibiotic art, such as the cephalosporins and penicillins and the nuclear analogues thereof.

Suitable radicals (R³' include conventional protecting or carboxyl blocking groups. The term "blocking group" as utilized herein is employed in the same manner and in accordance with the teaching of U.S. Pat. No. 3,697,515 which is incorporated herein by reference. Pharmaceutically acceptable derivatives of the present invention falling in this class are given below. Suitable blocking esters thus include those selected from the following list which is representative and not intended to be an exhaustive list of possible ester groups, wherein X'=O and R³' is given:

(i) $R^{3'}=CR^aR^bR^c$ wherein at least one of $R^a$, $R^b$ and $R^c$ is an electron-donor, e.g., p-methoxyphenyl. The remaining $R^a$, $R^b$ and $R^c$ groups may be hydrogen or organic substituting groups. Suitable ester groups of this type include p-methoxybenzyloxycarbonyl.

(ii) $R^{3'}=CR^aR^bR^c$ wherein at least one of $R^a$, $R^b$ and $R^c$ is an electron-attracting group, e.g., p-nitrophenyl, trichloromethyl, and o-nitrophenyl. Suitable esters of this type include p-nitrobenzyloxycarbonyl, and 2,2,2-trichloroethoxycarbonyl.

(iii) $R^{3'}=CR^aR^bR^c$ wherein at least two of $R^a$, $R^b$ and $R^c$ are hydrocarbon such as alkyl, e.g., methyl or ethyl, or aryl, e.g., phenyl and the remaining $R^a$, $R^b$ and $R^c$ group, if there is one, is hydrogen. Suitable esters of this type include t-butyloxycarbonyl, diphenylmethoxycarbonyl and triphenylmethoxycarbonyl.

Silyl esters, under this category of blocking groups, may conveniently be prepared from a halosilane of the formula: $R^4_3SiX'$ wherein X' is a halogen such as chloro or bromo and $R^4$ is alkyl, e.g., methyl, ethyl, t-butyl.

More generally stated, pharmaceutically acceptable carboxyl derivatives of the present invention are those derived by reacting I with alcohols, acylating reagents and the like. For example, esters and amides of interest are the above-listed starting materials and final products having the —COX'R³' group at the 3-position; wherein X' is oxygen, sulfur or NR' (R' is H or R³'), and R³' is alkyl having 1–6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1–6 carbon atoms and the alkylportion has 1–6 carbon atoms, such as pivaloyloxymethyl; haloalkyl wherein halo is chloro, and the alkyl portion is straight or branched having 1–6 carbon atoms, e.g., 2,2,2-trichloroethyl; alkenyl having 1–4 carbon atoms such as 2-propenyl, 3-butenyl, and 4-butenyl; aralkyl and lower alkoxyl- and nitro-substituted aralkyl such as benzyl, benzhydryl, o-nitrobenzyl, p-methoxybenzyl, and p-nitrobenzyl; phthalidyl; benzyloxyalkyl having 8–10 carbon atoms such as benzyloxymethyl, and (4-nitro) benzyloxymethyl.

In addition to the esters (and thio esters) listed above, amides are also embraced by the present invention, i.e., wherein X' is the

group. Representative of such amides are those wherein R' is selected from the group consisting of hydrogen and lower alkyl such as methyl and ethyl.

The most preferred -COX'R³' radicals of the present invention are those wherein (relative to Structure I above), X is oxygen and R is hydrogen; loweralkyl having 1–4 carbon atoms; lower alkenyl such as 3-methylbutenyl, 4-butenyl and the like; benzyl and substituted benzyl such as p-nitrobenzyl; pivaloyloxymethyl, 3-phthalidyl; and phenacyl.

The products of this invention (I) form a wide variety of pharmacologically acceptable salts with inorganic and organic bases; these include, for example, metal salts derived from alkali or alkaline earth metal hydroxides, carbonates or bicarbonates and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen-containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N-dibenzylethylenediamine, diethanolamine, piperazine, dimethylaminoethanol, 2-amino-2-methyl-1-propanol, theophylline, N-methylglucamine and the like. Acid addition salts, e.g., with hydrochloric, tartaric, hydrobromic, sulfuric, nitric, toluene-p-sulphonic and methane sulphonic acids may also be employed.

The salts can be mono-salts such as the monosodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The compounds of the present invention are valuable antimicrobial substances which are active against various gram-positive and gram-negative pathogens. Thus the free acid, free base, and especially the salts thereof such as amine and metal salts, particularly the alkali metal and alkaline earth metal salts, are useful bactericides and can be used for removing susceptible pathogens from dental and medical equipment for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules, suppositories, syrups, elixirs and the like which can be prepared in accordance with procedures well known in this art.

The novel compounds are valuable antibiotics active against various gram-positive and gram-negative bacteria, and accordingly, find utility in human and veterinary medicine. The compounds of this invention can therefore be used as antibacterial drugs for treating infections caused by gram positive or gram-negative bacteria, for example against *Staphylococcus aureus, Escherichia coli, Klebsiella pneumoniae, Bacillus subtilis, Salmonella typhosa,* Pseudomonas and *Bacterium proteus.* The antibacterials of the invention may further be utilized as additives to animal feedingstuffs, for preserving foodstuffs and disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 5 to about 600 mg. of active ingredient per kg. of body weight of the subject in one or more applications per day. A preferred daily dosage for adult humans lies in the range of from about 15 to 240 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following examples, illustrate but do not limit the product, process, compositional or method of treatment aspects of the present invention. All reaction temperatures are in °C.

EXAMPLE 1

Preparation of
4-methyl-4-(2-acetoxyvinyl)azetidinone-2-one

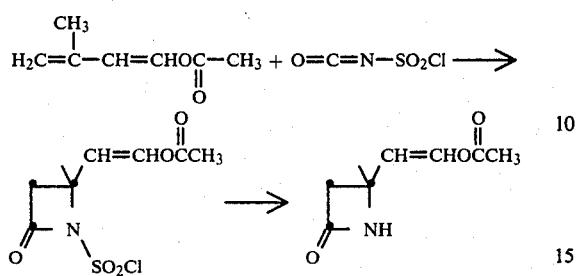

A solution of 1.0 ml distilled chlorosulfonylisocyanate (1.65 g; 11.7 mmoles) in 2.5 ml anhydrous diethyl ether is cooled under $N_2$ in a $-20°$ C. bath.

A solution of 1-acetoxy-3-methyl-butadiene (22 mmoles) in 2.5 ml anhydrous ether is similarly cooled under $N_2$ in a $-20°$ C. bath.

The chlorosulfonylisocyanate solution is added dropwise to the acetoxybutadiene solution by means of a Teflon tube immersed in the CSI solution and pressurized with $N_2$. The addition takes 10 minutes. Little or no color is seen and the reaction is stirred at $-20°$ C. for 0.5 hour. The solution is clear and has a light yellow color.

A solution of 2 g sodium sulfite and 5 g $K_2HPO_4$ in 20 ml $H_2O$ is prepared during the above 0.5 hour reaction time and is cooled in an ice bath; 20 ml of ether is added and the mixture is vigorously stirred in an ice bath. At the end of the 30 minute reaction time, the reaction mixture is transferred, again using $N_2$ pressure and the Teflon tube, from the reaction flask which is maintained in the $-20°$ C. bath, to the vigorously stirred hydrolysis mixture. Rapid dropwise addition is completed in 5 minutes. The hydrolysis is allowed to continue for 5 additional minutes. The hydrolysis mix has a pH of 6–8, preferably pH 8.

The phases are separated, leaving a yellowish-orange gum with the aqueous phase. The ether phase is dried directly with $MgSO_4$. The aqueous/gum phase is extracted three more times with 50 ml portions of ether, each being added to the initial ether/$MgSO_4$.

The dried extracts are filtered and concentrated under a $N_2$ stream to 5 ml.

A column of 10 g Baker silica gel, packed in ether is prepared, and the ether concentrate is applied to the top and run in. The flask/solids are rinsed three times with 2 ml ether, each being pipetted off and run into the column. Elution with ether gives the product.

EXAMPLE 2

Preparation of 4-methyl,
4-(2-acetoxyethyl)-2-azetidinone

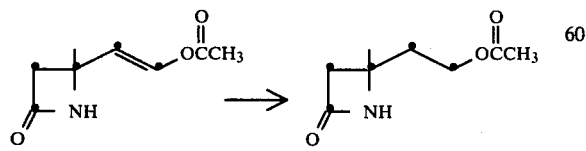

A solution of 4-methyl-4-(2-acetoxyvinyl)-2-azetidinone (10.0 g, 0.065 mole) in 200 ml ethyl acetate containing 100 mg of 10% Pd/C is hydrogenated on a Parr shaker at 25° C. under 40 psi hydrogen for 15 minutes. The mixture is filtered through a bed of Supercel and washed with additional ethyl acetate. The combined filtrate is evaporated in vacuo to give 4-methyl-4-(2-acetoxyethyl)-2-azetidinone.

EXAMPLE 3

Preparation of
4-methyl-4-(2-hydroxyethyl)-2-acetidinone

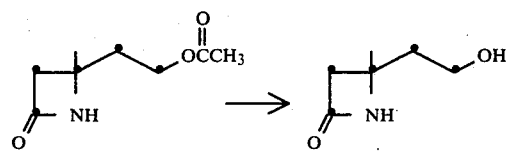

Under nitrogen at 0°, a solution of 4-methyl-4-(2-acetoxyethyl)-2-azetidinone (0.014 mole) in 25 ml anhydrous methanol is treated with a solution of sodium methoxide (77 mg, 1.4 mmoles) in 5 ml anhydrous methanol. After stirring for 1 hour, the solution is neutralized with glacial acetic acid. Removal of the methanol in vacuo gives crude 4-methyl-4-(2-hydroxyethyl)-2-azetidinone as an oil. The product is purified by chromatography on silica gel eluting with 10% MeOH/CHCl$_3$ to give the alcohol.

EXAMPLE 4

Preparation of
8-Oxo-2,2,6-trimethyl-3-oxa-1-azabicyclo[4.2.0]octane

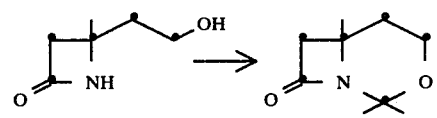

A solution of 4-methyl-4-(2-hydroxyethyl)-2-azetidinone (0.016 mole) and 2,2-dimethoxypropane (1.69 g, 0.016 mole) in 25 ml anhydrous methylene chloride is treated with boron trifluoride etherate (0.201 ml, 0.002 mole) at 25° C. The resulting solution is stirred for ten minutes. Removal of the solvent under reduced pressure and chromatography of the crude product on silica gel using 2:1 ethyl acetate/benzene as eluting solvent gives 8-oxo-2,2,6-trimethyl-3-oxa-1-azabicyclo[4.2.0]-octane.

EXAMPLE 4a

Preparation of
8-oxo-2,2,6-trimethyl-7-isopropyl-3-oxa-1-azabicyclo[4.2.0]octane

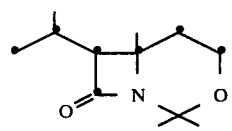

THF, 20 ml is placed under $N_2$, treated with 1.54 ml diisopropylamine and cooled to $-78°$ C. A solution of n-butyl lithium (1.97 M in hexane; 5.6 ml) is added dropwise over 5 min. The reaction mixture is stirred at $-78°$ C. for 10 min. and then treated with 8-oxo-2,2,6-trimethyl-3-oxa-1-azabicyclo[4.2.0]octane (0.0079 mmole) ml THF added dropwise over 5 min. After another 10 min.

hexamethylphosphoramide 1.97 ml is added. The mixture is stirred another 10 min., then treated with 2 ml of isopropyl iodide. The reaction mixture is stirred at −78° C. for 15 min. and allowed to warm to 25° C. and stirred for 15 min. The reaction mixture is diluted with EtOAc, washed once with pH 7 phosphate buffer then dried and evaporated. The residue is chromatographed on silica gel using 25% EtOAc/C₆H₆ as eluant to give 8-oxo-2,2,6-trimethyl-7-isopropyl-3-oxa-1-azabicyclo[4.2.0]-octane.

EXAMPLE 4b

Preparation of 8-oxo-2,2,6,7-tetramethyl-3-oxa-1-azabicyclo[4.2.0]octane

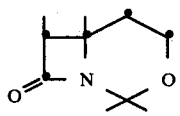

Following the procedure of Example 4a, except substituting an equivalent amount of methyl iodide for the isopropyl iodide, the title compound is obtained.

EXAMPLE 5

Preparation of 8-oxo-2,2,6,7-tetramethyl-7-(hydroxymethyl)-3-oxa-1-azabicyclo[4.2.0]octane

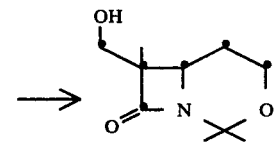

To a solution of 1.1 equivalents of freshly prepared lithium diisopropylamide in anhydrous tetrahydrofuran under a nitrogen atmosphere at −78° is added a solution of 8-oxo-2,2,6,7-tetramethyl-3-oxa-1-azabicyclo[4.2.0]octane in anhydrous tetrahydrofuran which has been cooled to −78° C. After two minutes, the resulting lithium enolate is treated with excess formaldehyde, introduced as a gas just above the surface of the stirred solution. The solution is stirred for 30 minutes at −78° and then poured into water. The aqueous phase is saturated with sodium chloride and extracted with ethyl acetate. The combined ethyl acetate solutions are dried over magnesium sulfate and filtered. The filtrate is evaporated under reduced pressure to give the crude product. Purification by chromatography on silica gel using ethyl acetate/benzene gives 8-oxo-2,2,6,7-tetramethyl-7-(hydroxymethyl)-3-oxa-1-azabicyclo[4.2.0]octane.

EXAMPLE 6

Preparation of 8-oxo-2,2,6,7-tetramethyl-7-(p-nitrobenzylcarbonyldioxymethyl)-3-oxa-1-azabicyclo[4.2.0]octane

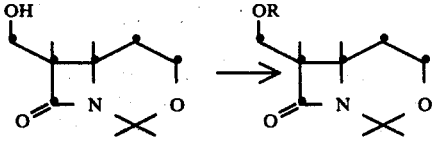

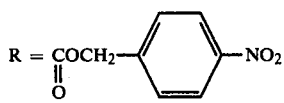

Under anhydrous conditions at 0° C. a solution of 8-oxo-2,2,6,7-tetramethyl-7-(hydroxymethyl)-3-oxa-1-azabicyclo[4.2.0]octane (0.302 mmole) in 0.6 ml ether is treated with powdered potassium hydroxide (19 mg, 0.332 mmole). After a period of 15 minutes, p-nitrobenzyl chloroformate (65 mg, 0.302 mmole) is added to the reaction mixture. Stirring is continued at 25° C. for an additional 15 hours. The mixture is partitioned between 1 M pH 7 phosphate buffer and more ether. The ether phase is washed with water and brine, dried over magnesium sulfate and filtered. Evaporation of the filtrate under reduced pressure, followed by purification by preparative thick layer chromatography on silica gel developing with 1:9 ethyl acetate/benzene gives 8-oxo-2,2,6,7-tetramethyl-7-(p-nitrobenzylcarbonyldioxymethyl)-3-oxa-1-azabicyclo[4.2.0]octane.

EXAMPLE 7

Preparation of 3,4-dimethyl-3-(p-nitrobenzylcarbonyldioxymethyl)-4-(2-hydroxyethyl-2-azetidinone

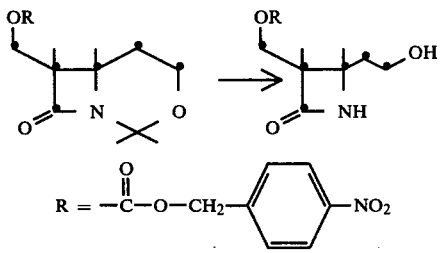

8-Oxo-3-oxa-2,2,6,7-tetramethyl-7-(1-p-nitrobenzylcarbonyldioxymethyl)-1-azabicyclo[4.2.0]octane (ca.1 g) is dissolved in 8 ml acetic acid and 2 ml water and heated at 65° C. for 1.25 hours. The acetic acid and water are removed under reduced pressure and the residue is taken up in benzene and evaporated to give 3,4-dimethyl-3-(p-nitrobenzylcarbonyldioxymethyl)-4-(2-hydroxyethyl)-2-azetidinone.

EXAMPLE 8

Preparation of 3-(2-aminoethylthio)-5,6-dimethyl-6-(hydroxymethyl)-7-oxo-1-azabicyclo[3.2.0]hept-2-ene-2-carboxylic acid Step A

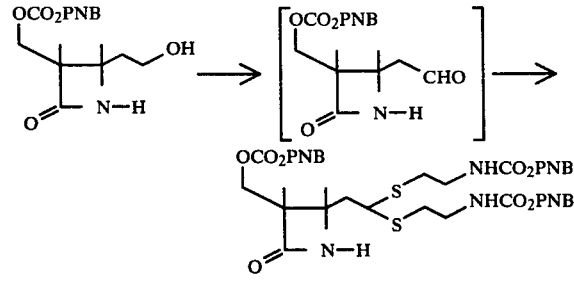

-continued

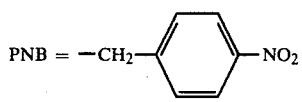

To 6.75 ml anhydrous pyridine (mw=79; ρ=0.982; 83.9 mmole) in 350 ml anhydrous acetonitrile is added 4.05 g anhydrous powdered chromium trioxide (mw=100; 40.5 mmole). After stirring at room temperature (25° C.) for 30 minutes, 9.6 g dried Supercell is added and stirring is continued for 5 additional minutes. A solution of 3,4-dimethyl-3-(p-nitrobenzylcarbonyldioxymethyl)-4-(2-hydroxyethyl)-2-azetidinone (9.5 mmole) in 30 ml anhydrous acetonitrile is added all at once. The reaction mixture is stirred under anhydrous conditions at room temperature (25° C.) for one hour. Addition of 9.6 g NaHSO$_3$ is followed by 5 minutes of stirring after which the reaction mixture is filtered through a mixed packed bed of 40 g silica gel and 40 g anhydrous magnesium sulfate. The bed is washed repeatedly with acetonitrile (total volume of filtrate ~600 ml). The filtrate is concentrated under a N$_2$ stream to 130 ml total volume. To this solution containing crude aldehyde at 0° C. under N$_2$ is added 9.64 g p-nitrobenzyloxycarbonylaminoethanethiol (mw=256; 37.7 mmole) as prepared below (Example 8, Step B). To the stirred reaction mixture is added 8.0 ml boron trifluoride etherate (mw=142; ρ=1.125; 63.4 mmole). After 1.5 hours at 0° C., the reaction mixture is poured into a stirred ice-cold mixture of 69 g K$_2$HPO$_4$-500 ml H$_2$O and 700 ml ethyl acetate (EA). The layers are separated, and the aqueous one is saturated with NaCl and re-extracted with additional EA. The combined organic layers are washed twice with brine, dried over anhydrous MgSO$_4$ and filtered. The filtrate is concentrated under a N$_2$ stream and then pumped on high vacuum to give crude 1.

The material is chromatographed on 450 g silica gel (column height=48 cm; diameter=5.5 cm) packed and applied in CHCl$_3$ and eluted with increasing percentages of MeOH in CHCl$_3$ (0-4% MeOH/CHCl$_3$). Those fractions containing the desired product are combined, concentrated under a N$_2$ stream; and pumped on high vacuum to give 1.

Step B

Preparation of
p-Nitrobenzyloxycarbonylaminoethanethiol

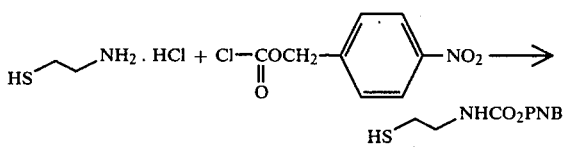

To 600 ml diethyl ether (Et$_2$O)-75 ml H$_2$O in an ice bath with stirring is added 3.2 g cysteamine hydrochloride (mw=114; 28.1 mmole). A solution of 7.14 g NaHCO$_3$ (mw=84; 85 mmole) in 75 ml H$_2$O is added. The ice bath is removed, and at room temperature a solution of 6.75 g p-nitrobenzylchloroformate (mw=216; 31.3 mmole) in 270 ml Et$_2$O is added dropwise over a period of one hour. After 10 additional minutes, the layers are separated. The ether layer is extracted with 150 ml 0.25 N HCl, and then with 200 ml brine. Each aqueous layer is then backwashed successively with 100 ml Et$_2$O. The combined Et$_2$O layers are dried over anhydrous MgSO$_4$, filtered, and concentrated under a N$_2$ stream. The crystalline residue is slurried in a small amount of ether, filtered, and the pale yellow crystals are dried under high vacuum to give 4.7 g p-nitrobenzyloxycarbonylaminoethanethiol (65% yield).

NMR (CDCl$_3$) 8.18 (d, J=8 Hz, aromatic protons ortho to nitro), 7.47 (d, J=8 Hz, aromatic protons meta to nitro), 5.27 (—N$\underline{H}$—), 5.20 (s, —C$\underline{H}_2$—φ—pNO$_2$), 3.40 (m, —C$\underline{H}_2$—NH—), 2.67 (m, —C$\underline{H}_2$—SH), 1.35 (t, J=8.5 Hz, —S$\underline{H}$) in ppm downfield from TMS.

IR (CHCl$_3$ solution) carbonyl- ~1725 cm$^{-1}$

M.S.—molecular ion-256, (M-47) at 209, (M-136) at 120, $^+$CH$_2$φpNO$_2$ at 136.

Step C

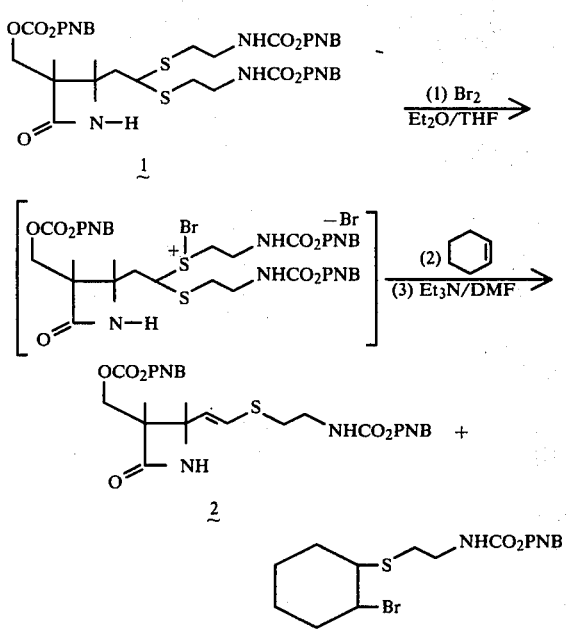

To 14.2 ml pentane (dried over 4 A Linde molecular sieves) is added 0.5 ml Br$_2$ (mw=160; 9.75 mmole). To 6.02 mmole of 1 in 58 ml tetrahydrofuran (THF) (freshly distilled from lithium aluminum hydride) (LAH) and 65 ml Et$_2$O (dried over 3 A 1/16" Linde molecular sieves) at 0° C. under N$_2$ with stirring is added dropwise 10 ml of the above 0.66 M Br$_2$ solution (6.6 mmole). After 10 minutes at 0° C., 0.67 ml cyclohexene (mw=82; ρ=0.81; 6.6 mmole) is added. After 5 minutes at 0° C., 1.7 ml triethylamine (mw=101; ρ=0.729; 12.3 mmole) is added immediately followed by 40 ml ice-cold dimethylformamide (DMF) (distilled from anhydrous CaSO$_4$ at 40 mm and stored over 4 A Linde molecular sieves). The ice bath is removed, and stirring is continued for 2¼ hours at room temperature. The reaction mixture is poured into a stirred ice-cold mixture of 12.6 ml 1 M KH$_2$PO$_4$ 160 ml H$_2$O-500 ml (EA). After separation of the layers, the aqueous one is saturated with sodium chloride and re-extracted with EA. The combined organic layers are extracted once with brine, dried over anhydrous MgSO$_4$, filtered and concentrated under a N$_2$ stream followed by pumping under high vacuum to provide crude 2.

The material is chromatographed on 250 g silica gel (height=45 cm; diameter=4.5 cm) packed and applied in CHCl$_3$ and eluted with increasing percentages of MeOH in CHCl₃ (0–3% MeOH/CHCl₃). Those fractions containing clean product are combined, concentrated under a N₂ stream, and pumped on high vacuum to give 2. Contaminated fractions are rechromatographed on silica gel using increasing percentages of EA in CHCl₃ (0–25% EA/CHCl₃) to give additional 2.

STEP D

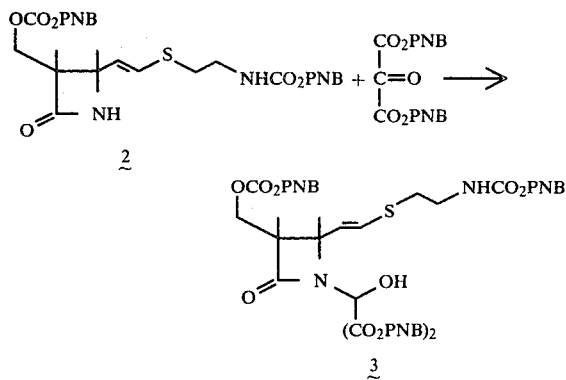

To a stirred solution of 2.48 g di(p-nitrobenzyl) ketomalonate (from Example 8, Step E) (mw=388; 6.39 mmole) in 400 ml hot anhydrous toluene is added a solution of 4.39 mmole of 2 in 20 ml THF (distilled from LAH) and 40 ml anhydrous toluene. After some of the solvent is boiled off, additional anhydrous toluene is added, and the azeodrying process is repeated three times. The solution is then refluxed under N₂ for 30 minutes. Additional toluene is then allowed to boil off yet the volume is not allowed to diminish so much that precipitation occurs. Total heating time is approximately 2½ hours. The clear yellow reaction mixture is removed from the oil bath and placed under a stream of N₂ which instantaneously causes clouding. After concentration to a yellow oil, the residue is dissolved in CH₂Cl₂, dried over anhydrous MgSO₄, filtered, and concentrated under a N₂ stream to give crude 3.

The material is chromatographed on 250 g silica gel packed and applied in CHCl₃ (height=43 cm; diameter=4.5 cm). Elution with 500 ml 0.5% MeOH/CHCl₃ is followed by continued elution with 1% MeOH/CHCl₃ for the remainder of the chromatography. After the emergence of excess reagent, those fractions containing pure 3 are combined, concentrated under a N₂ stream and then on high vacuum to give 3.

Later fractions containing 3 and the corresponding cis thioenol ether are re-chromatographed on silica gel to give additional 3.

Step E

Preparation of di-p-Nitrobenzyl Ketomalonate

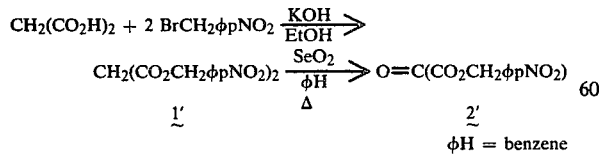

φH = benzene

A mixture of 100 g p-nitrobenzyl bromide (0.46 mole), 28.6 g malonic acid (0.275 mole) and 750 ml ethanol (EtOH) is stirred and warmed on the steam bath until solution is achieved. A solution of 33 g KOH (>85% purity; ~0.6 mole) in 200 ml of water is added carefully with swirling. An additional 200 ml of water is added, and the two-phase system is refluxed for 1.8 hours. The lighter color homogeneous solution is cooled in ice for 1 hour and the crude product isolated by filtration, washed twice with a minimum of cold EtOH, and dried by pulling dry N₂ through the cake; 33.7 g of solid is obtained. If, during the refluxing stage the reaction mixture is slowly concentrating to ca. half volume by allowing refluxing solvent to distill off, the crude product yield rises to 77 g. The material is recrystallized from methanol to give pure di-p-nitrobenzyl malonate 1'.

A mixture of 23.4 g of 1', 10 g SeO₂, and 30–40 ml of xylene is stirred in a flask immersed in an oil bath. The bath temperature is raised over 1 hour to 130°–135°. A gradual darkening of the reaction mixture is noted, and after a total of 4 hours at 130°–135°, most of the insoluble residue is black Se°. The mixture is cooled, MgSO₄ is added to remove the water, and Celite is added to aid in filtration. The mixture is filtered through Celite and the cake washed with xylene and a small portion of EtOAc. Final volume: 60 ml. A 100 g column of Baker Silica Gel is prepared in benzene and 10 ml of filtrate applied, then eluted with increasing amounts of EtOAc in benzene, 500 ml fractions being collected. After one 2% ethyl acetate (EtOAc)/φH, and two 10% EtOAc/φH fractions, the third 10% and first 20% EtOAc/φH provide the bulk of the product (~1.6 g from 10 ml filtrate) as judged by tlc (20% EtOAc/CHCl₃; silica gel GF). Recrystallization from benzene, (1 g in ca. 50 ml concentrated to ~⅓ volume and "spiked" with 1 ml of H₂O saturated benzene): provides 0.24 g 2'; mp(117) 121°–122°.

Step F

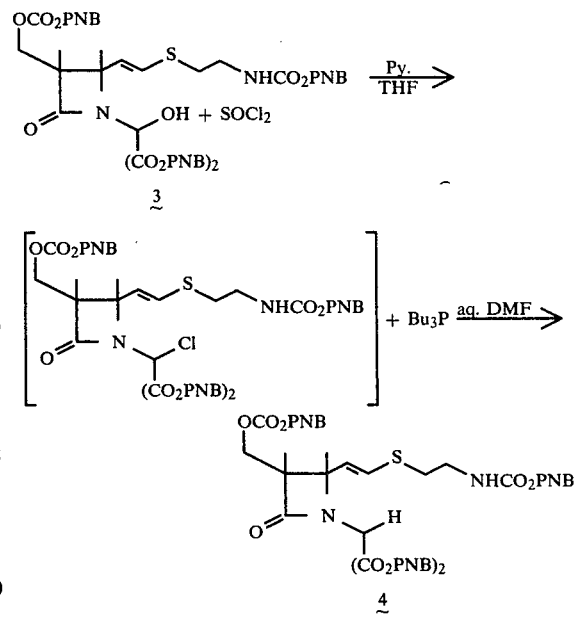

A solution of 1.53 mmoles of 3 in CH₂Cl₂ is dried over anhydrous MgSO₄, filtered, concentrated under a N₂ stream, and dried further under high vacuum just prior to the following reaction. To a solution of 3 in 24 ml THF (freshly distilled from LAH) at −20° C. is added 0.206 ml anhydrous pyridine (mw=79; ρ=0.982;

2.56 mmole). With stirring under N₂, 294 mg of freshly distilled thionyl chloride (mw=119; 2.47 mmole) in 5 ml THF is added dropwise. The reaction mixture is stirred for 10 minutes at −20° C., then ½ hour at 0° C. and finally 1 hour at 25° C. The pyridine hydrochloride is filtered under N₂ and washed with 20 ml THF. The filtrate is concentrated under a N₂ stream followed by pumping on high vacuum. The resulting foam is swirled in 25 ml anhydrous THF, and a small amount of insoluble material is filtered off under N₂. The filtrate is reconcentrated as above to a foam.

To this freshly prepared chloro compound is added with stirring a freshly shaken suspension of 678 mg tributylphosphine (mw=202; 3.36 mmole) in 36.5 ml 9:1 DMF-H₂O followed by 294 mg K₂HPO₄ (mw=174; 1.69 mmole). The reaction mixture is stirred at 25° C., for 35 minutes. After dilution with 120 ml EA and 60 ml brine, the layers are separated, and the aqueous one is extracted two times with EA. The combined organic layers are washed one time with brine, dried over anhydrous MgSO₄, filtered and concentrated under a N₂ stream followed by pumping on high vacuum to give crude 4.

The material is chromatographed on 100 g silica gel (height=28.5 cm; d=4 cm) packed and applied in CHCl₃ and eluted with 0.5% MeOH in CHCl₃. Those fractions containing clean product are combined, concentrated under a N₂ stream and then on high vacuum to give 4. Contaminated fractions are re-chromatographed on silica gel thin layer plates (eluant=50% acetone/hexane; extraction of desired u.v. band with CHCl₃ and EA to provide additional 4.

Step G

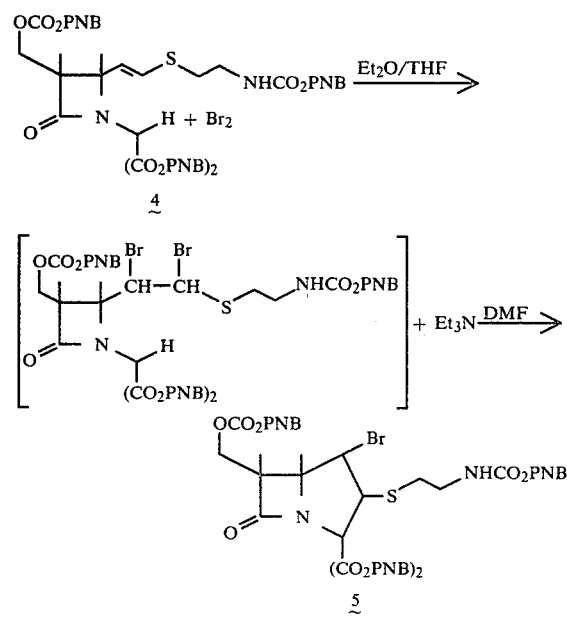

To 8.5 ml pentane (dried over 4A Linde molecular sieves) is added 0.2 ml Br₂ (mw=160; 3.9 mmole). To 0.746 mmoles of 4 in 18 ml THF (freshly distilled from LAH) and 5.7 ml Et₂O (dried over 3A 1/16" Linde molecular sieves) at 0° C. under N₂ with stirring is added dropwise 1.8 ml of the above 0.45 M Br₂ solution (0.81 mmole). After 15 minutes at 0° C., 0.42 ml triethyl amine (mw=101;ρ=0.729; 3.03 mmole) is added immediately followed by 10.5 ml ice-cold DMF (distilled from CaSO₄ at 40 mm and stored over 4A Linde molecular sieves). The ice-bath is removed, and stirring at room temperature is continued for 2 hours. The reaction mixture is poured into a stirred ice-cold mixture of 3.1 ml 1 M KH₂PO₄—70 ml H₂O—100 ml EA. The layers are separated, and the aqueous one is saturated with NaCl and re-extracted with EA. The combined organic layers are washed once with brine, dried over anhydrous MgSO₄, and filtered. The filtrate is concentrated under a N₂ stream and then pumped on high vacuum to give crude 5.

The material is chromatographed on 60 g silica gel (diameter=2.8 cm) packed and applied in CHCl₃ and is eluted with 100 ml-2% EA/CHCl₃; 100 ml-4% Ea/CHCl₃ and then 5% EA/CHCl₃ for the remainder of the chromatography. The fractions containing pure 5 are combined, concentrated under a N₂ stream, and pumped on high vacuum to give 5.

Step H

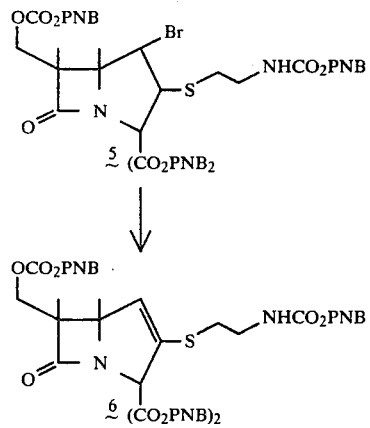

To 29 mg anhydrous silver fluoride (mw=127; 0.23 mmole) is added a solution of 0.14 mmole of 5 in 3.5 ml anhydrous pyridine. The stoppered reaction mixture is stirred at room temperature in the dark for one hour and then poured into 20 ml cold water—30 ml EA. After separation of the layers, the aqueous one is extracted two times with EA and one time with CHCl₃. Each organic layer is extracted one time with H₂O and one time with brine. The combined organic layers are dried over anhydrous MgSO₄, filtered, and concentrated under a N₂ stream followed by pumping on high vacuum to give crude 6.

Preparative thin layer chromatography (eluant=40% acetone/hexane; repeated extraction of desired u.v. band with a large volume of CHCl₃) yields slightly contaminated 6. Re-chromatographing on silica using EA in CHCl₃ as an eluting system gives 6.

Step I

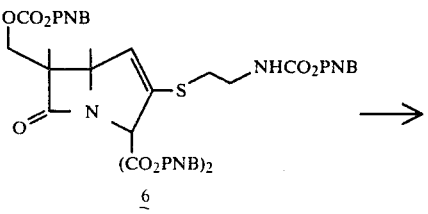

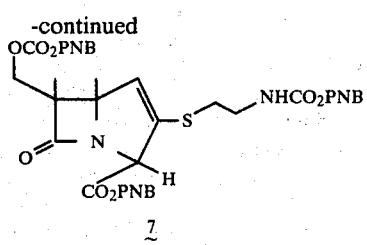

A solution of 0.082 mmole of 7 in 0.9 ml S-collidine (distilled from powdered KOH ~30 mm pressure) is added to 13.4 mg anhydrous LiI (dried for few hours at 100° C. over $P_2O_5$ under vacuum) (mw=134; 0.1 mmole). With stirring under $N_2$, the reaction mixture is heated in an oil bath at 120° C. After a total of 30 minutes, the reaction mixture is cooled to 25° C., diluted with $CH_2Cl_2$, and transferred to a round bottom flask for concentration under a $N_2$ stream and then on high vacuum. Partitioning the residue between EA-$H_2O$ and 1 ml 1 M $KH_2PO_4$ is followed by extraction of the aqueous layer two additional times with EA and one time with $CHCl_3$. Each organic layer is then backwashed with brine. The combined organic layers are dried over anhydrous $MgSO_4$, filtered, concentrated under a $N_2$ stream and then on high vacuum to give crude 7.

Preparative thin layer chromatography on silica gel (plate is eluted two times with 40% acetone/hexane; repeated extraction of the appropriate u.v. bands with large volume of $CHCl_3$) yields recovered starting material and 7.

Step J

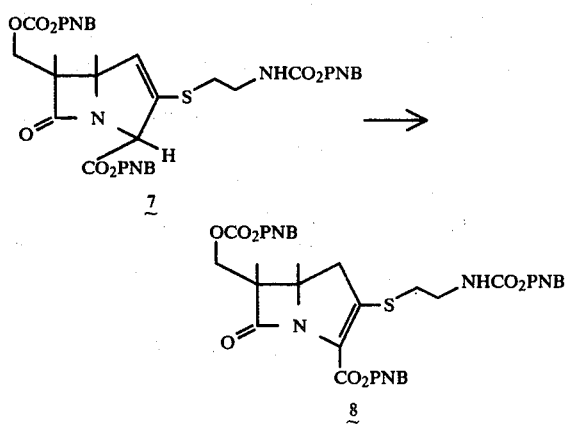

To 0.064 mmole of 7 in 0.7 ml DMSO (distilled from $CaH_2$ at 8 mm and stored over 4 A Linde molecular sieves) is added 100 μl dissopropylamine (distilled from NaH under $N_2$ and stored over 4 A Linde molecular sieves) (mw=101; ρ=0.722; 0.71 mmole). The stoppered reaction mixture is stirred for a few minutes and then allowed to stand for 2 hours. The amine and most of the DMSO are then concentrated off under high vacuum with no external heating. The residue is passed quickly through a column of silica gel (packed, applied, and eluted with EA) to remove residual DMSO. After concentration under a $N_2$ stream of all fractions having u.v. absorbance, the material is chromatographed on a thin layer silica gel plate (eluant=50% EA/$CHCl_3$; repeated extraction of desired u.v. bands with a large volume of chloroform). Recovered starting material is re-submitted to the reaction conditions and isolation procedure two more times to yield additional 8.

Step K

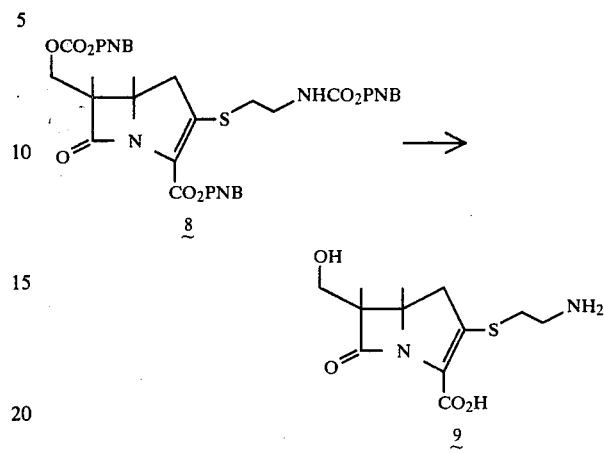

To ca.5 mg 8 is added 0.60 ml dioxane, 0.05 ml ethanol, 0.35 ml deionized water and 0.01 ml of 1.0 M $K_2HPO_4$. To the resultant clear solution is added 5 mg of 10% Pd/C. The suspension is flushed with $N_2$, then 5-6 times alternately with 50 psi $H_2$ and vacuum. Finally, it is shaken under a 50 psi $H_2$ atmosphere for 30-40 min. After centrifugation, the Pd/C is washed and centrigufed 2-3 X with 0.5 ml portions of deionized water. The combined centrifugates are extracted 5×1-2 ml ether. Residual ether is removed under vacuum and the aqueous solution applied to an XAD-2 column (20×140 mm). Fractions of 100 drops (6-7 ml) are collected, with continuous UV monitoring, by elution with deionized water. Emergence of strongly UV absorbing material begins around fractions 3-5 and is usually complete by fractions 25-30. Early fractions are examined by UV to exclude those few deemed too strongly absorbing in the 270-280 mμ region. The remaining fractions are combined and lyophilized. The residue is evaluated by dissolving in 10.0 ml of deionized water and measuring the UV absorption at 298 mμ.

EXAMPLE 9

Step A

Preparation of [1-(t-butyldimethylsilyl)-4-methyl-4-vinyl-2-azetidinone]

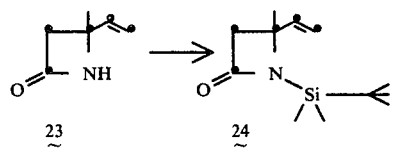

A solution of 23 [4-methyl-4-vinyl-2-azetidinone] (11.89 mmoles) and triethylamine (1.82 ml, 13.08 mmoles) in anhydrous N,N-dimethylformamide is placed under a nitrogen atmosphere, cooled to 0° C. and treated with t-butyldimethylchlorosilane (1.885 g., 12.48 mmoles) resulting in the immediate appearance of a heavy white precipitate. This mixture is stirred for one hour while gradually warming to room temperature. The mixture is partitioned between 30 ml methylene chloride and 90 ml cold 1 M potassium dihydrogen phosphate. The aqueous phase is extracted with 20 ml methylene chloride. The combined organic phases are washed four times with 30 ml portions of water and finally with 50 ml brine. The methylene chloride solution is dried over anhydrous magnesium sulfate and filtered. The filtrate is evaporated under reduced pressure to give 24 [1-(t-butyldimethylsilyl)-4-methyl-4-vinyl-2-azetidinone].

Step B

Preparation of 4-methyl-[1-(t-butyldimethylsilyl)-3-(hydroxymethyl)-4-vinyl-2-azetidinone]

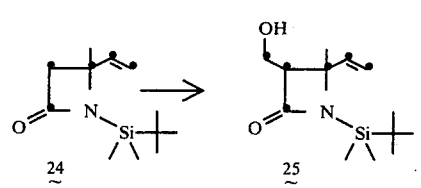

To a solution of freshly prepared lithium diisopropylamide (7.82 mmoles) in 36 ml anhydrous tetrahydrofuran under a nitrogen atmosphere at −75° C. is added a solution of 4-methyl-[1-(t-butyldimethylsilyl)-4-vinyl-2-azetidinone], 24, (1.60 g, 7.11 mmoles) in 10 ml anhydrous THF. The resulting yellow solution of the lithium enolate is, after 16 minutes, treated with excess formaldehyde (see Example 5, above). In 10 minutes, the reaction is quenched by adding 30 ml of a saturated aqueous ammonium chloride solution. This mixture is extracted with 50 ml and 25 ml portions of ethyl acetate. The combined ethyl acetate solutions are washed with 50 ml of brine and dried over anhydrous magnesium sulfate. The drying agent is removed by filtration and the filtrate is evaporated in vacuo to give the crude product. Purification by chromatography on silica gel eluting with 10% ethyl acetate/chloroform gives 4-methyl-[1-(t-butyldimethylsilyl)-3-hydroxymethyl)-4-vinyl-2-azetidinone], 25.

Step C

Preparation of 4-methyl-1-(t-butyldimethylsilyl)-3-(1-p-nitrobenzylcarbonyldioxymethyl)-4-vinyl-2-azetidinone

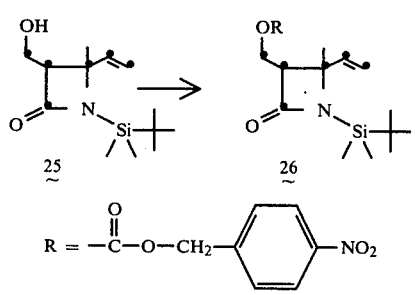

Under nitrogen at −78° C. a solution of 25 (56 mg, 0.220 mmole) in 1 ml of anhydrous tetrahydrofuran is treated with 2.4 M n-butyllithium in hexane (101 μl, 0.242 mmole). To this solution is added, in five minutes, a solution of p-nitrobenzyl chloroformate (52 mg, 0.242 mmole) in anhydrous tetrahydrofuran. After stirring at −78° C. for a period of 55 minutes, 10 ml of a saturated aqueous ammonium chloride solution is added and the product extracted into ethyl acetate. The combined ethyl acetate solutions are washed with brine and dried over anhydrous magnesium sulfate. The drying agent is removed by filtration, and the filtrate is evaporated in vacuo to give crude 26. Purification by preparative thicklayer chromatography on silica gel developing with 5% ethyl acetate/chloroform gives 26.

Step D

Desilylation of 26 to provide 27 [4-methyl-3-(p-nitrobenzylcarbonyldioxymethyl)-4-vinyl-2-azetidinone]

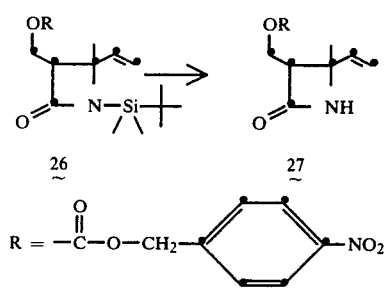

A solution of 26 [1-(t-butyldimethylsilyl)-4-methyl-3-p-nitrobenzylcarbonyldioxymethyl)-4-vinyl-2-azetidinone] (61 mg, 0.141 mmole) in 2 ml of 0.5 N HCl/MeOH is stirred at room temperature (25° C.) for a period of 3 hours. The solution is then cooled to 0° C. and neutralized by the addition of 5 ml of 5% aqueous sodium bicarbonate. The product is extracted into ethyl acetate (10 ml, 2×5 ml). The combined ethyl acetate solutions are washed with water (2×5 ml) and 10 ml brine and then dried over anhydrous magnesium sulfate. The drying agent is removed by filtration, and the filtrate is evaporated in vacuo to give an oil. Preparative thick-layer chromatography of this material on silica gel developing with 10% ethyl acetate/chloroform gives 4-methyl-3-(p-nitrobenzylcarbonyldioxymethyl)-4-vinyl-2-azetidinone, 27.

Step E

Preparation of 14 via 28 by sulfenyl halide addition and dehydrohalogenation

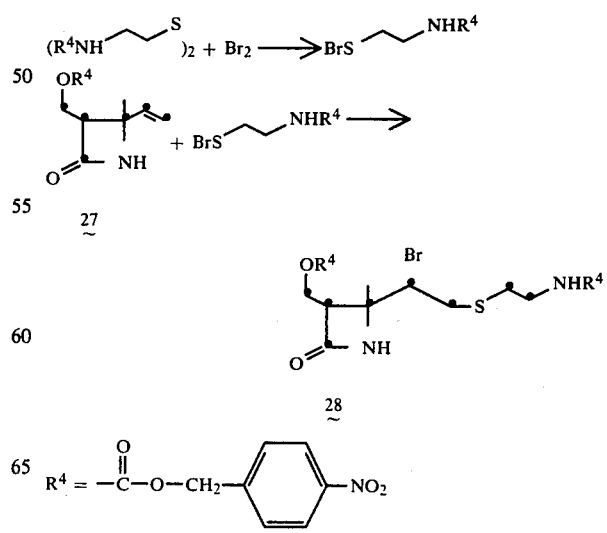

A solution of the N-p-nitroCBZ cysteamine disulfide, 96 mg (0.19 mmoles) in 1.5 ml THF (freshly distilled from LiAlH₄) is cooled to −25° C. and treated dropwise with stirring with 0.5 ml of a solution of 135 mg Br₂ in sieve dried CCl₄ (2.2 ml final volume; portion added is equivalent to 0.19 mmoles of Br₂). The resultant orange solution is stirred at −20° C. for 5 min. then treated with 54.0 mg of the vinyl azetidinone, 27, in 0.5 ml sieve dried CH₂Cl₂. The color lightens to yellow. The mixture is allowed to come to 0° C. over 5–10 minutes. Examination by tlc (silica 5% MeOH in CH₂Cl₂ or 20% EtOAc in CH₂Cl₂) shows a main spot with R$_f$ and Ce$^{IV}$+/H+/heat characteristics different from either disulfide or starting 4-vinyl-2-azetidinone. The reaction mixture is concentrated to 0.5 ml under N₂, streaked directly on two 8"×8" 1000μ silica GF plates, and developed with 20% EtOAc in CH₂Cl₂. The main band under U.V., is scraped off, and extracted with EtOAc to give 28.

Step F

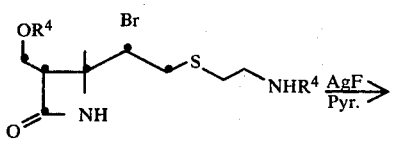

28

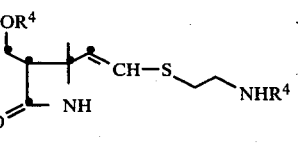

14

Treatment with 1.01 g. AgF(mw=127; 7.95 mmole) of 4.2 mmole of 28 in 34 ml. pyridine at room temperature (22° C.) in the dark under N₂ for 1 hr. is followed by concentration of the entire reaction mixture under high vacuum and with a water bath at 25°–30° C. to a brown-black residue. After chasing a few times with CHCl₃, the residue is slurried in CH₂Cl₂ and run through a short column of silica gel (eluting with 2% MeOH/CH₂Cl₂) thus removing most of the silver salts. The fractions containing product are combined. Chromatography on silica gel (1% MeOH/CH₂Cl₂) provides the desired product 14. Preparative thin layer chromatography on silica gel of column fractions which still contained less polar impurities (2.5% MeOH/CH₂Cl₂), provides additional product.

EXAMPLE 10

Preparation of Bis (p-Nitrobenzyloxycarbonylaminoethyl)disulfide

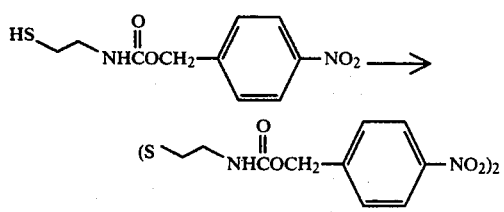

Under nitrogen at −20° C., bromine (1.21 ml, 0.022 mmole) is added to a solution of p-nitrobenzyloxycarbonylaminoethanethiol (11.28 g, 0.044 mole) in 100 ml of anhydrous tetrahydrofuran. The cooling bath is removed, and the cold solution is stirred for 15 minutes. The solution is then diluted with 400 ml ethyl acetate and washed with 200 ml 1 M pH 7 phosphate buffer, 200 ml 1 M dibasic potassium phosphate, water (2×200 ml, 100 ml) and 200 ml brine. It is dried over anhydrous magnesium sulfate and filtered. The filtrate is evaporated in vacuo giving a yellow solid residue. This material is chromatographed on silica gel eluting with 5% ethyl acetate/chloroform to give 10.5 g of crystalline bis (p-nitrobenzyloxycarbonylaminoethyl)disulfide:

IR (CH₂Cl₂)μ: 3.04 NH 5.96 carbonyl 6.22, 6.61 nitro NMR (CDCl₃)δ:

| NMR (CDCl₃) ∂ : | 8.24 | } d, J=8.5Hz, ArH |
|---|---|---|
| | 7.54 | |

5.37, broad s, NH 5.26, s, ArCH₂O 3.60, q, J=6 Hz and 6 Hz, NHCH₂CH₂ 2.86, t, J=6 Hz, NHCH₂CH₂S

EXAMPLE 11

Preparation of 8-oxo-2,2,6-trimethyl-7-(1-hydroxy-2-phenylethyl)-3-oxa-1-azabicyclo[4.2.0]octane

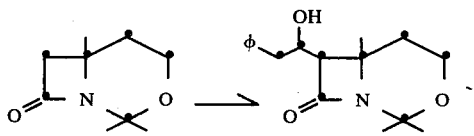

Following the procedure of Example 5, except that instead of formaldehyde, an equivalent amount of phenylacetaldehyde is used, and instead of 8-oxo-2,2,6,7-tetramethyl-3-oxa-1-azabicyclo[4.2.0]octane, 8-oxo-2,2,6-trimethyl-3-oxa-1-azabicyclo[4.2.0]octane is used, upon purification by silica gel chromatography, the title compound is obtained.

EXAMPLE 12

Preparation of 3-(2-aminoethylthio)-6-(1-hydroxy-2-phenylethyl)-5-methyl-7-oxo-1-azabicyclo(3.2.0)hept-2-ene-2-carboxylic acid

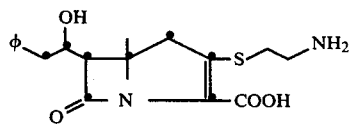

Following the procedures of Examples 6, 7, and 8 except that 8-oxo-2,2,6-trimethyl-7-(1-hydroxy-2-phenylethyl)-3-oxa-1-azabicyclo[4.2.0]octane is substituted in equivalent amount for its analogous substrate, the title compound is obtained.

EXAMPLE 13

Preparation of 8-oxo-2,2,6-trimethyl-7-benzyl-3-oxa-1-azabicyclo[4.2.0]octane

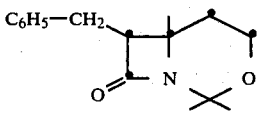

Following the procedure described for the preparation of 8-oxo-3-oxa-2,2,6-trimethyl-7-isopropyl-1-azabicyclo[4.2.0]octane from 8-oxo-3-oxa-2,2,6-trimethyl-1-azabicyclo[4.2.0]-octane (Example 4a, above) and using benzyl bromide instead of isopropyl iodide there is obtained 8-oxo-2,2,6-trimethyl-7-benzyl-3-oxa-1-azabicyclo[4.2.0]octane.

EXAMPLE 14

Preparation of 8-oxo-2,2,6-trimethyl-7-benzyl-7-(1-hydroxyethyl)-3-oxa-1-azabicyclo[4.2.0]octane

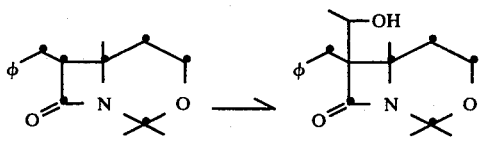

Using the procedure of Example 5 but substituting an equivalent amount of 8-oxo-2,2,6-trimethyl-7-benzyl-3-oxa-1-azabicylo[4.2.0]octane (Example 13) for 8-oxo-2,2,6,7-tetramethyl-3-oxa-1-azabicyclo[4.2.0], and an equivalent amount of acetaldehyde for formaldehyde, there is obtained, upon purification by silica gel chromatography, the title compound.

EXAMPLE 15

Preparation of 4-(2,2-(bisbenzylthio)ethyl)-4-methyl-3-(p-nitrobenzylcarbonyldioxymethyl)-2-azetidinone

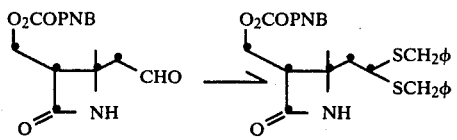

When in Example 8, Step A, an equivalent amount of benzyl mercaptan is substituted for 2-(p-nitrobenzyloxycarbonylamino)ethane thiol, the title compound is obtained.

EXAMPLE 16

Preparation of 4-methyl-4-(2,2-(bis-o-nitrobenzylthio)ethyl)-3-(nitrobenzylcarbonyldioxymethyl)-2-azetidinone

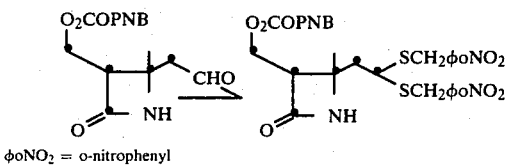

φoNO₂ = o-nitrophenyl

When in Example 8, Step A, an equivalent amount of o-nitrobenzylthiol is substituted for 2-(p-nitrobenzyloxycarbonylamino)ethane thiol, the title compound is obtained.

EXAMPLE 17

Preparation of 4-methyl-3-(p-nitrobenzylcarbonyldioxymethyl)-4-[1-bromo-2-(2-p-nitrobenzyloxycarbonylamino)1,1-dimethylethylthio)ethyl]-2-azetidinone

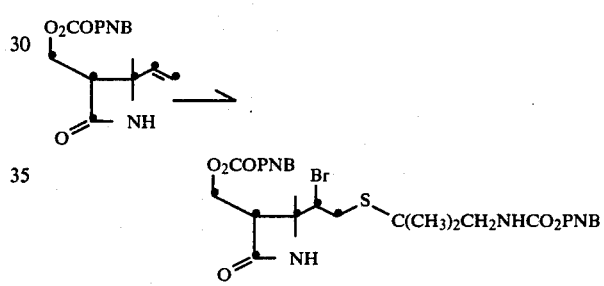

If in Example 9, Step E, an equivalent solution of 2-(p-nitrobenzyloxycarbonylamino)-1,1-dimethylethylsulfenyl bromide, prepared by cleavage of bis(2-p-nitrobenzyloxycarbonylamino)-1,1-dimethylethylthio)mercury with bromine in THF/ether at 0° C., is substituted for the solution of 2-(p-nitrobenzyloxycarbonylamino)ethylsulfenyl bromide, the title compound is obtained.

EXAMPLE 18

Preparation of 3-benzylthio-5-methyl-6-hydroxymethyl-7-oxo-1-azabicyclo[3.2.0]hept-2-ene-2-carboxylic acid

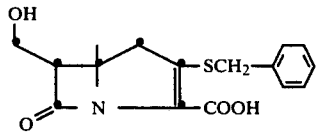

Following the procedure of Example 8, Steps B-K except substituting for the indicated azetidinone the azetidinone of Example 15 the title compound is obtained.

EXAMPLE 19

Preparation of 3-(2-amino-1,1-dimethylethylthio)-5-methyl-6-hydroxymethyl-7-oxo-1-azabicyclo[3.2.0]hept-2-ene-2-carboxylic acid

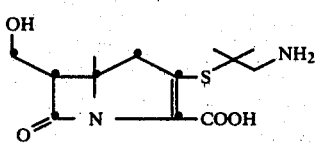

Following the procedure of Example 9, Step F, except substituting for the indicated azetidinone the azetidinone of Example 17, followed by the reactions corresponding to those of Example 8 Steps D-K, the title compound is obtained.

EXAMPLE 20

Preparation of 3-mercapto-5-methyl-6-(p-nitrobenzylcarbonyldioxymethyl)-7-oxo-1-azabicyclo-[3.2.0]hept-2-ene-2-carboxylic acid, p-nitrobenzyl ester

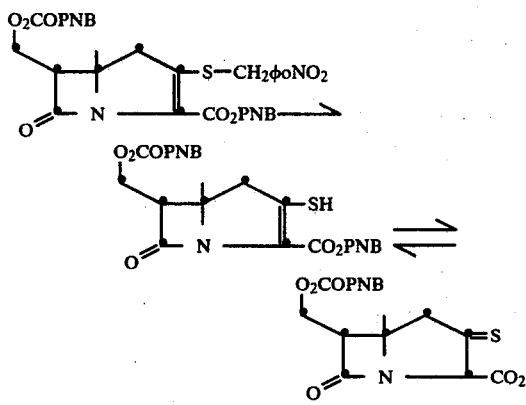

A solution of 5 mg of 1 (prepared from the azetidinone of Example 16 and the procedure of Example 8) in 0.6 ml of dioxane is irradiated for one hour in a quartz vessel under nitrogen with nitrogen being slowly bubbled through (1 bubble per 5 sec.) using 300 nm sources in a Rayonet apparatus, to give the title compound as a mixture of thiol-thione tautomers.

EXAMPLE 21

Preparation of 5-Methyl-6-(hydroxymethyl)-3-mercapto-7-oxo-1-azabicyclo[3.2.0]hept-2-ene-2-carboxylic acid

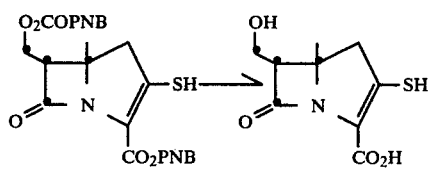

If the solution obtained after irradiation in Example 20 is immediately treated with 0.05 ml of ethanol, 0.35 ml deionized water, 0.01 ml of 1.0 M $K_2HPO_4$, and 5 mg of 10% Pd/C and then treated as in Example 8, Step K, except that instead of purification on the XAD-2 column the ether extracted aqueous solution is cooled in ice, carefully acidified to pH 2 and extracted with ethyl acetate, and the combined extracts then washed once with saturated NaCl solution, dried with $MgSO_4$ and concentrated under a stream of $N_2$, the title compound is obtained.

EXAMPLE 22

Following the procedure of the foregoing Examples and text, the following representative compounds of the present invention (Table I) are obtained by analogy.

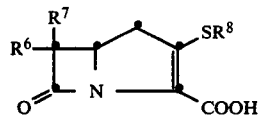

For every entry in Table I, the butadiene reagent is given by the general formula

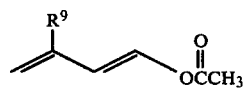

wherein $R^9$ is defined in Table I.

TABLE 1

| Compound | $R^8$ | $R^6$ | $R^7$ | $R^9$ |
|---|---|---|---|---|
| 1. | —$(CH_2)_3NH_2$ | H | $CH_2OH$ | —$CH_3$ |
| 2. | —$(CH_2)_3NHC(=NH)H$ | H | $CH_2OH$ | —$CH_3$ |
| 3. | —$(CH_2)_3NHC(=NH)CH_3$ | H | $CH_2OH$ | —$CH_3$ |
| 4. | —C$_6$H$_4$—$CH_2NH_2$ | H | $CH_2OH$ | —$CH_3$ |
| 5. | —C$_6$H$_4$—$CH_2NHC(=NH)H$ | H | $CH_2OH$ | —$CH_3$ |

TABLE 1-continued

| Compound | $R^8$ | $R^6$ | $R^7$ | $R^9$ |
|---|---|---|---|---|
| 6. | 4-(CH₂NHC(=NH)CH₃)-C₆H₄-CH₂- | H | CH₂OH | CH₃ |
| 7. | 3-(CH₂NH₂)-C₆H₄-CH₂- | H | CH₂OH | -CH₂CH₃ |
| 8. | 3-(CH₂NHC(=NH)H)-C₆H₄-CH₂- | H | CH₂OH | -CH₂CH₂CH₃ |
| 9. | 4-(CH₂NHC(=NH)CH₃)-C₆H₄-CH₂- | H | CH₂OH | cyclopropyl |
| 10. | 2-methyl-1,3,4-thiadiazol-5-yl | H | CH₂OH | cyclopropylmethyl |
| 11. | -CH(CH₃)-CH₂-NH₂ | H | CH₂OH | CH₃ |
| 12. | -CH₃ | H | CH₂OH | -CH₂CH₂CH₂CH₃ |
| 13. | -C₆H₅ (phenyl) | H | CH₂OH | cyclohexylmethyl |
| 14. | 1-methyl-tetrazol-5-yl | H | CH₂OH | CH₃ |
| 15. | -CH₂CH(NH₂)CH₃ | H | CH₂OH | 4-Cl-C₆H₄-CH₂- |
| 16. | -CH₂C(NH₂)(CH₃)CH₃ | H | CH₂OH | 4-OCH₃-C₆H₄-CH₂- |
| 17. | pyridin-4-yl-methyl | H | CH₂OH | CH₃ |
| 18. | -CH₂CH₂NH₂ | H | CH₃CH(NH₂)- | CH₃ |
| 19. | -φ | CH₃ | CH₃CH(NH₂)- | CH₃ |
| 20. | -CH₂CH₂CH₂NH₂ | CH₃ | CH₃CH(OH)- | CH₃ |
| 21. | -φ | CH₃ | CH₂OH | -CH(CH₃)₂ |
| 22. | CH₂CH₂NH₂ | H | (CH₃)₂CHCH₂CH(OH)- | cyclopropylmethyl |
| 23. | CH₂CH₂NH-C(=NH)-H | H | (CH₃)₂CHCH₂CH(OH)- | cyclobutyl |
| 24. | CH₂CH₂NH-C(=NH)-CH₃ | H | (CH₃)₂CHCH₂CH(OH)- | -CH₂CH₂CH₂CH₃ |
| 25. | CH₂CH₂NH₂ | CH₃ | (CH₃)₂CHCH₂CH(OH)- | CH₃ |
| 26. | CH₂CH₂NH-C(=NH)-H | CH₃ | (CH₃)₂CHCH₂CH(OH)- | CH₃ |
| 27. | CH₂CH₂NH-C(=NH)-CH₃ | CH₃ | " | CH₃ |

TABLE 1-continued

| Compound | R⁸ | R⁶ | R⁷ | R⁹ |
|---|---|---|---|---|
| 28. | CH₂CH(CH₃)NH₂ | CH₃ | " | CH₃ |
| 29. | CH₂CH₂NH₂ | H | cyclopropyl-CH(OH)- | CH₃ |
| 30. | " | CH₃ | " | cyclopropyl-CH(OH)- (n-propyl) |
| 31. | CH₂CH₂NH·C(=NH)H | H | " | cyclobutyl |
| 32. | CH₂CH₂NH-C(=NH)-CH₃ | H | " | cyclopropyl |
| 33. | CH₂CH₂NHC(=NH)-H | H | φCH₂CH₂C(OH)- | CH₂-cyclopropyl |
| 34. | CH₂CH₂NHC(=NH)CH₃ | H | " | isopropyl |
| 35. | CH(CH₃)₂CH₂NH₂ | H | " | cyclopentyl |
| 36. | φ | H | CF₃CH(OH)- | CH₃ |
| 37. | 1-methyl-tetrazol-5-yl | H | cyclopropyl-CH₂CH(OH)- | CH₃ |
| 38. | CF₃ | H | CH₃CH(OH)- | CH₃ |
| 39. | CH₂CH₂NH₂ | H | " | |
| 40. | CH₂CH₂N(morpholino) | H | 1,3-dioxolan-2-yl-CH(OH)- | CH₃ |
| 41. | CH₂CH₂NH₂ | H | CH₂-CH₂-CH(OH) | 4-Cl-phenyl |
| 42. | CH₂CO₂CH₃ | H | CH₃CH(OH)- | cyclopentyl-CH₂- |
| 43. | 4-(CH₂NH₂)-phenyl | H | CH₃CH(OH)- | CH₃ |
| 44. | 5-methyl-1,3,4-thiadiazol-2-yl | H | 2-hydroxycyclopentyl | CH₃ |
| 45. | pyridyl | H | HOCH₂CH₂- | CH₃ |
| 46. | pyridyl | H | MeON=CH·CH₂- | CH₃ |
| 47. | 1-(CH₂NH₂)-tetrazol-5-yl | H | HOCH(CH₂-CH₂)- | CH₂-cyclopropyl |
| 48. | 3-phenyl-5-methyl-isoxazol-4-yl | H | (CH₃)₂CHCH₂CH(OH)- | CH₃ |
| 49. | 2-(CH₂NH₂)-1,3,4-thiadiazol-5-yl | CH₃ | " | CH₃ |
| 50. | CH₂CH₂OH | H | φCH₂CH₂C(OH)- | n-propyl |

TABLE 1-continued

| Compound | R⁸ | R⁶ | R⁷ | R⁹ |
|---|---|---|---|---|
| 51. | $CH_2CH_2NH_2$ | H | $\phi CH_2CH_2\underset{\underset{CO_2H}{\mid}}{\overset{\overset{OH}{\mid}}{CH}}-$ | 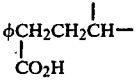 |
| 52. | $CH_2CH_2NH_2$ | H |  | $CH_3$ |
| 53. | $CH_2CH_2NH_2$ | H | 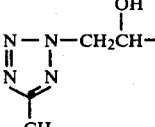 | $-CH_2-$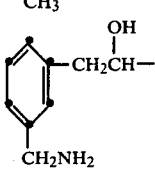 |
| 54. |  | H | " | $CH_3$ |
| 55. |  | $CH_3$ | " | $CH_3$ |
| 56. | " | H |  | 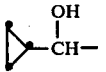 |
| 57. | " | H |  | 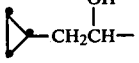 |
| 58. | $\underset{CH_2CH_2NH\overset{\overset{NH}{\|}}{C}CH}{}$ | H |  | $-CF_3$ |
| 59. | $CH_2CH_2NH_2$ | H | " | $CF_3$ |
| 60. | " | $CH_3$ | " | $CH_3$ |
| 61. | $\underset{CH_2CH_2NH\overset{\overset{NH}{\|}}{C}H}{}$ | $CH_3$ | " | $CH_3$ |
| 62. | $\underset{CH_2CH_2NH\overset{\overset{NH}{\|}}{C}CH_3}{}$ | $CH_3$ | " | $CH_3$ |
| 63. | $\underset{CH_2CH_2NH\overset{\overset{NH}{\|}}{C}H}{}$ | H | $CH_3CH_2\overset{\overset{OH}{\|}}{CH}-$ |  |
| 64. | $\underset{CH_2CH_2NH\overset{\overset{NH}{\|}}{C}CH_3}{}$ | H | " | 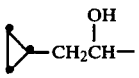 |
| 65. | $CH_2CH_2NH_2$ | $CH_3$ | " |  |
| 66. | $\underset{CH_2CH_2NH\overset{\overset{NH}{\|}}{C}CH_3}{}$ | $CH_3$ | " | 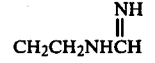 |
| 67. | $\underset{CH_2CH_2NH\overset{\overset{NH}{\|}}{C}H}{}$ | $CH_3$ | " | $CH_3$ |
| 68. | $\underset{CH_2CH_2NH\overset{\overset{NH}{\|}}{C}CH_3}{}$ | H | $\phi CH_2CH_2\overset{\overset{OH}{\|}}{CH}-$ | $CH_3$ |
| 69. | $\underset{CH_2CH_2NH\overset{\overset{NH}{\|}}{C}H}{}$ | H | " | $CH_3$ |
| 70. | " | H | $\phi \underset{\underset{CO_2H}{\mid}}{CH}CH_2\overset{\overset{OH}{\mid}}{CH}-$ | $CH_3$ |
| 71. | 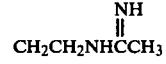 | $CH_3$ | $\phi \underset{\underset{CO_2H}{\mid}}{CH}CH_2\overset{\overset{OH}{\mid}}{CH}-$ | $CH_3$ |
| 72. | " | " | $\phi CH_2CH_2\overset{\overset{OH}{\mid}}{CH}-$ | $CH_3$ |
| 73. | " | " | $(CH_3)_2CH\overset{\overset{OH}{\mid}}{CH}-$ | $CH_3$ |

TABLE 1-continued

| Compound | R⁸ | R⁶ | R⁷ | R⁹ |
|---|---|---|---|---|
| 74. | " | " | (CH₃)₂CH—CH₂CH(OH)— | CH₃ |
| 75. | " | " | CH₃CH₂CH(OH)— |  |
| 76. | CF₃ | " | HOCH₂CH₂— | 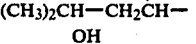 |
| 77. | " | " | (CH₃)₂CHCH₂CH(OH)— |  |
| 78. | " | " | (CH₃)₂CHCH(OH)— | CH₃ |
| 79. | " | " | φCH₂CH₂CH(OH)— | CH₃ |
| 80. | " | " | φCH(CO₂H)CH₂CH(OH)— | 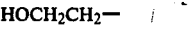 |
| 81. | " | " | -CH(OH)— |  |
| 82. | " | " | -CH₂CH(OH)— | 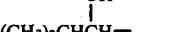 |
| 83. | " | " | CF₃CH(OH)— | CF₃ |
| 84. | " | H | " | CF₃ |
| 85. | " | H | HOCH₂CH₂— | CF₃ |
| 86. | CF₃ | H | -CH(OH)— | CH₃ |
| 87. | " | " | φ—CH(CO₂H)CH₂CH(OH)— | CH₃ |
| 88. | " | " | φCH₂CH₂CH(OH)— | 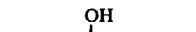 |
| 89. | " | " | (CH₃)₂CHCH(OH)— |  |
| 90. | " | " | (CH₃)₂CHCH₂CH(OH)— | 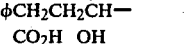 |
| 91. |  | " | " | CH₃ |
| 92. | " | " | CH₃CH₂CH(OH)— | CH₃ |
| 93. | " | " | (CH₃)₂CHCH(OH)— |  |
| 94. | " | " | φCH₂CH₂CH(OH)— |  |
| 95. | " | " | φCH₂CH₂CH(OH)(CO₂H)— | 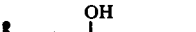 |
| 96. | " | " | -CH(OH)— |  |
| 97. | " | " | CF₃CH(OH)— |  |
| 98. | " | " | HOCH₂CH₂— | 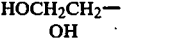 |
| 99. | —CH₂NH₂ | CH₃ | CF₃CH(OH) | CH₃ |

TABLE 1-continued

| Compound | R⁸ | R⁶ | R⁷ | R⁹ |
|---|---|---|---|---|
| 100. | [thiazole with CH₃, S, N-N] | " | " | " |
| 101. | " | H | " | " |
| 102. | " | " | cyclopropyl-CH₂CH(OH)- | " |
| 103. | " | " | cyclopropyl-CH(OH)- | " |
| 104. | " | " | (CH₃)₂CH-CH(OH)- | " |
| 105. | " | " | HOCH₂CH₂- | " |
| 106. | " | CH₃ | (CH₃)₂CH-CH(OH)- | " |
| 107. | " | " | HOCH₂CH₂- | " |
| 108. | " | " | cyclopropyl-CH(OH)-CH- | " |
| 109. | " | " | cyclopropyl-CH₂CH(OH)- | " |
| 110. | " | " | φCHCH₂CH(OH)- with CO₂H | " |
| 111. | " | " | φCH₂CH₂CH(OH)- | " |
| 112. | " | " | (CH₃)₂CHCH(OH)- | " |
| 113. | " | " | (CH₃)₂CHCH₂CH(OH)- | " |
| 114. | [pyridyl] | H | " | " |
| 115. | " | " | (CH₃)₂CHCH(OH)- | " |
| 116. | " | " | φCH₂CH₂CH(OH)- | cyclopropyl |
| 117. | " | " | φCHCH₂CH(OH)- with CO₂H | n-butyl |
| 118. | " | " | cyclopropyl-CH(OH)- | cyclopropyl (△) |
| 119. | " | " | cyclopropyl-CH₂CH(OH)- | cyclobutyl (□) |
| 120. | " | " | CH₃CH(OH)- | n-pentyl |
| 121. | " | " | CH₃CH₂CH(OH)- | phenyl |
| 122. | " | CH₃ | CH₃CH(OH)- | " |
| 123. | " | " | cyclopropyl-CH₂CH(OH)- | " |
| 124. | " | " | cyclopropyl-CH(OH)-CH₃ | " |
| 125. | CH₂CH₂NHC(=NH)CH₃ | " | " | " |
| 126. | " | CH₃ | " | CF₃ |

TABLE 1-continued

| Compound | R⁸ | R⁶ | R⁷ | R⁹ |
|---|---|---|---|---|
| 127. | CH₂CH₂NHC(=NH)—H | " | " | " |
| 128. | CH₂CH₂NH₂ | " | " | " |
| 129. | " | H | CF₃CH(OH)— | CH₃ |
| 130. | CH₂CH₂NH—C(=NH)CH₃ | " | " | CH₃ |
| 131. | CH₂CH₂NHCH(=NH) | " | " | " |
| 132. | " | CH₃ | " | " |
| 133. | CH₂CH₂NHC(=NH)CH₃ | " | " | " |
| 134. | CH₂CH₂NH₂ | " | " | " |
| 135. | " | " | HO—CHCH₂— | " |
| 136. | CH₂CH₂NHC(=NH)CH₃ | " | " | " |
| 137. | CH₂CH₂NHCH(=NH) | " | " | " |
| 138. | " | H | " | " |
| 139. | CH₂CH₂NHC(=NH)CH₃ | " | " | " |
| 140. | (cyclopentadienyl)—CH₂NH₂ | " | " | " |
| 141. | " | CH₃ | " | " |
| 142. | (cyclopentadienyl)—CH₂NH—C(=NH)—CH₃ | " | HO—CH₂CH₂— | 4-OCH₃-C₆H₄— |
| 143. | (cyclopentadienyl)—CH₂NHCH(=NH) | " | " | " |
| 144. | (cyclopentadienyl)—CH₂NH₂ | H | CF₃CH(OH)— | " |
| 145. | 1-methyl-tetrazol-5-yl | CH₃ | CH₃CH(OH)CH— | C₆H₅ |
| 146. | " | " | (cyclopropyl)—CH(OH)CH₂— | C₆H₅ |
| 147. | " | " | (cyclopropyl)—CH(OH)— | 4-Cl-C₆H₄— |
| 148. | " | " | CF₃CH(OH)— | CH₃ |
| 149. | " | " | φCH₂CH₂CH(OH)— | " |
| 150. | " | " | φCHCH₂CH(OH)—, CO₂H | " |
| 151. | " | " | (CH₃)₂CHCH(OH)— | " |
| 152. | " | " | (CH₃)₂CHCH₂CH(OH)— | " |
| 153. | 1-methyl-tetrazol-5-yl | " | HOCH₂CH₂— | CH₃ |

TABLE 1-continued

| Compound | R⁸ | R⁶ | R⁷ | R⁹ |
|---|---|---|---|---|
| 154. | ![S-CH3 thiadiazole]  -S-C(=N-N=)-CH₃ | H | $CH_3CH_2\underset{\underset{OH}{|}}{CH}-$ | " |
| 155. | " | " | $\phi CH_2CH_2\underset{\underset{OH}{|}}{CH}-$ | " |
| 156. | " | " | $\phi CH\ CH_2\underset{\underset{OH}{|}}{CH}-$ $\overset{|}{CO_2H}$ (on $\phi CH$) | " |

EXAMPLE 23

Preparation of the N-Formimidoyl derivative of 3-(2-aminoethylthio) 5,6-dimethyl-6-(hydroxymethyl)-7-oxo-1-azabicyclo[3.2.0]hept-2-ene-2-carboxylic acid

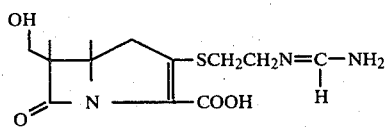

Compound 9 from Example 8, Step K (544 mg) is dissolved in pH 7 0.1 N phosphate buffer (25 ml) and cooled in an ice bath with magnetic stirring. The solution is adjusted to pH 8.5 using 2.5 N sodium hydroxide solution dispensed from an automatic burette. While maintaining a pH of 8.5, methyl formimidate hydrochloride (711 mg) is added portionwise over 2–3 minutes. After an additional 10 minutes, the pH of the solution is brought to 7.0 using 2.5 N hydrochloric acid. The solution is chromatographed on a column of XAD-2 resin (150 cc) which is eluted with water. The N-formimidoyl derivative is eluted and lyophilized.

Following the procedure of Example 23 enhanced product isolation is achieved when the XAD-2 column is replaced by an otherwise equivalent column of Dowex 50-X4 (Na+ cycle, 200–400 mesh).

Amidine embodiments of the present invention, such as that illustrated in Example 23 represent a preferred class. With reference to the generic representation of the compounds of the present invention (Structure I, above), such embodiments are possible when the radical —SR⁸ bears an amino functional group. The preparation of amidine and amidine-like species is fully described in copending, commonly assigned U.S. Patent Application Ser. No. 852,425 (filed Nov. 17, 1977), now U.S. Pat. No. 4,194,047, which application is incorporated herein by reference to the extent that it describes the preparation of amidine and amidine-like derivatives from species of the present invention which carry an amino group on —SR⁸.

EXAMPLE 24

Preparation of the N-Acetimidoyl derivative of 3-(2-aminoethylthio) 5,6-dimethyl-6-(hydroxymethyl)-7-oxo-1-azabicyclo[3.2.0]hept-2-ene-2-carboxylic acid

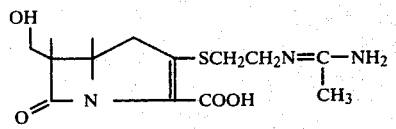

Compound 9 from Example 8, Step K (200 mg) is dissolved in pH 7 0.1 N phosphate buffer (13 ml) and cooled in an ice bath with magnetic stirring. The solution is adjusted to pH 8.5 using 2.5 N sodium hydroxide solution dispensed from an automatic burette. While maintaining a pH of 8.5, ethyl acetimidate hydrochloride (400 mg) is added portionwise over a few minutes. After an additional 40 minutes the solution is adjusted to pH 7.0 with 2.5 N hydrochloric acid. The solution is then chromatographed on Dowex 50-X8 resin (250 cc, Na+ cycle, 100–200 mesh) and is eluted with water. The N-acetimidoyl derivative is eluted and lyophilized.

EXAMPLE 25

Preparation of Silylated 3-(2-aminoethylthio)-5,6-dimethyl-6-(hydroxymethyl)-7-oxo-1-azabicyclo[3.2.0]hept-2-ene-2-carboxylic acid

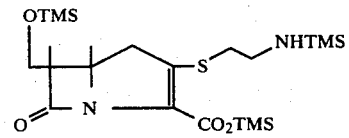

Compound 9 from Example 8, Step K (84 mg) is suspended in 40 ml tetrahydrofuran (THF) under a N₂ atmosphere and is concentrated to 10 ml; hexamethyldisilazene (1.0 ml) and trimethylchlorosilane (300 μl) is added. The mixture is reacted for 20 mins. at 25° C. with vigorous stirring. The suspension is then centrifuged to remove ammonium chloride. The supernatant is evaporated to provide the title compound under a nitrogen stream for future reaction.

EXAMPLE 26

Preparation of the N-Piperidin-1-yl Methylene Derivative of 3-(2-aminoethylthio) 5,6-dimethyl-6-(hydroxymethyl)-7-oxo-1-azabicyclo[3.2.0]hept-2-ene-2-carboxylic acid

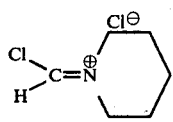

Silylated product from above example  ⟶

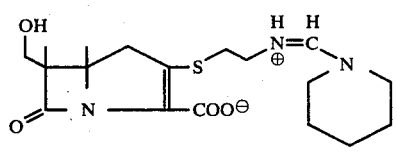

Compound 9 from Example 8, Step K (170 μmol) is silylated according to the procedure previously described. The silylated antibiotic is dissolved in methylene chloride (6 cc) in a septum stoppered flask under positive nitrogen pressure and cooled in a dry ice-acetone bath. To the magnetically stirred solution is added a solution (180 μl) of triethylamine (644 μmol) in methylene chloride. This is followed by the addition of a solution of chloropiperidinomethylium chloride (67 mg, 405 μmol) in methylene chloride (465 μl). After 1 hour in the dry ice bath, the reaction solution is rapidly added to a tetrahydrofuran −pH 7, 0.1 N phosphate buffer (1:1) solution (50 ml). The mixture is then concentrated under vacuum to 10 ml to give a homogeneous solution. The solution is washed twice with ethyl acetate (2×5 ml) and ether (2×5 ml) and briefly pumped under vacuum. This aqueous solution is then chromatographed on an XAD-2 resin column (60 ml bed). The product is eluted in 10% aqueous tetrahydrofuran (following water elution) to give the captioned product.

EXAMPLE 27

Preparation of the N'-Tert-Butyl-N-Formimidoyl derivative of 3-(2-aminoethylthio)-5,6-dimethyl-6-(hydroxymethyl)-7-oxo-1-azabicyclo[3.2.0]hept-2-ene-2-carboxylic acid

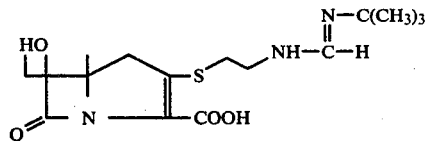

Compound 2 from Example 8, Step K (110 mg) is dissolved in pH 7 0.1 N phosphate buffer (5 ml) and to this is added a solution of ethyl N-tert-butyl formimidate (290 mg) in tetrahydrofuran (1 ml). The pH of the solution is adjusted to and maintained at 8.5 using an autoburette dispensing 1 N NaOH. After 30 minutes, the pH is adjusted to 7.0 with 2.5 N HCl. The solution is chromatographed on an ice water jacketed column of Dowex 50-X4 resin (53 cc, Na+ cycle, 200–400 mesh) and eluted with deionized water. The fractions containing the title product are combined and lyophilized.

EXAMPLE 28

Preparation of Pharmaceutical Compositions

One such unit dosage form consists in mixing 120 mg of 1:

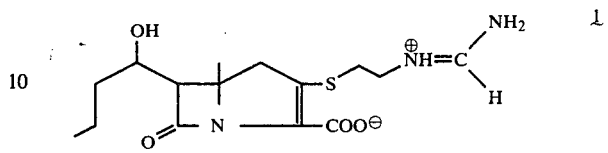

with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules and should it be necessary to mix more than 145 mg of ingredients together, larger capsules such as compressed tablets and pills can also be prepared. The following examples are illustrative of the preparation of pharmaceutical formulations:

| TABLET | PER TABLET |
|---|---|
| 1 | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg. |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| | PER TABLET |
|---|---|
| PARENTERAL SOLUTION | |
| Ampoule: | |
| 1 | 500 mg. |
| Diluent: Sterile Water for Injection | 2 cc. |
| OPTHALMIC SOLUTION | |
| 1 | 100 mg. |
| Hydropropylmethyl Cellulose | 5 mg. |
| Sterile Water | to 1 ml. |
| OTIC SOLUTION | |
| 1 | 100 mg. |
| Benzalkonium chloride | 0.1 mg. |
| Sterile Water | to 1 ml. |
| TOPICAL OINTMENT | |
| 1 | 100 mg. |
| Polyethylene Glycol 4000 U.S.P. | 400 mg. |
| Polyethylene Glycol 400 U.S.P. | 1.0 gram |

What is claimed is:

1. A compound having the structure:

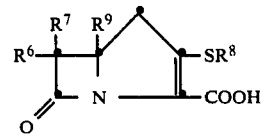

and the pharmaceutically acceptable salts thereof; wherein $R^6$ is selected from the group consisting of hydrogen and loweralkyl; $R^7$ is selected from the group consisting of: hydroxyloweralkyl which may be substituted with cycloloweralkyl, phenyl, trifluoromethyl, dioxolane, carboxyl, methyltetrazole and aminomethylphenyl and aminoloweralkyl; $R^8$ is selected from the group consisting of hydrogen, loweralkyl which may be substituted with amino, formamidino, acetamidino, guanidino, loweralkanoyl, hydroxy, halo and morpholane, phenyl which may be substituted with aminomethyl, formamidinomethyl and acetamidinomethyl, methylthiadiazole, methyltetrazole, pyridine, aminomethylthiadiazole and aminomethyltetrazole; and $R^9$ is selected from the group consisting of loweralkyl, cycloloweralkyl, cycloloweralkylloweralkyl, phenyl, halophenyl, loweralkoxyphenyl and trifluoromethyl; and wherein $R^7$ is not 1-hydroxyethyl when $R^6$ is hydrogen and $R^8$ is 2-aminoethyl.

2. A compound according to claim 1 wherein $R^9$ is selected from the group consisting of loweralkyl, cycloloweralkyl, cycloloweralkylloweralkyl, phenyl and loweralkoxyphenyl; $R^8$ is selected from the group consisting of aminoloweralkyl, formamidinoloweralkyl, acetamidinoloweralkyl and guanidinoloweralkyl; $R^7$ is selected from the group consisting of hydroxyloweralkyl which may be substituted with cycloloweralkyl, phenyl, carboxyl, trifluoromethyl, dioxalane, methyltetrazole and aminomethylphenyl; and $R^6$ is selected from the group consisting of hydrogen and methyl.

3. A compound according to claim 2 wherein $R^9$ is selected from the group consisting of methyl, ethyl, propyl, isopropyl, cyclopropyl, cyclobutyl, cyclohexyl, cyclopropylmethyl and methoxyphenyl.

4. A compound according to claim 2 wherein $R^8$ is selected from the group consisting of aminoethyl, formamidinoethyl, acetamidinoethyl and guanidinoethyl.

5. A compound according to claim 1 selected from the group consisting of:

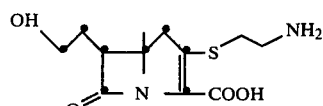

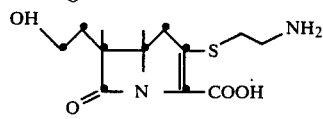

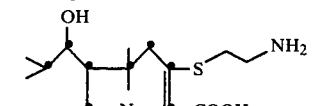

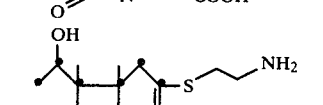

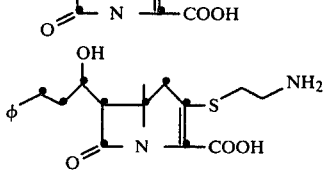

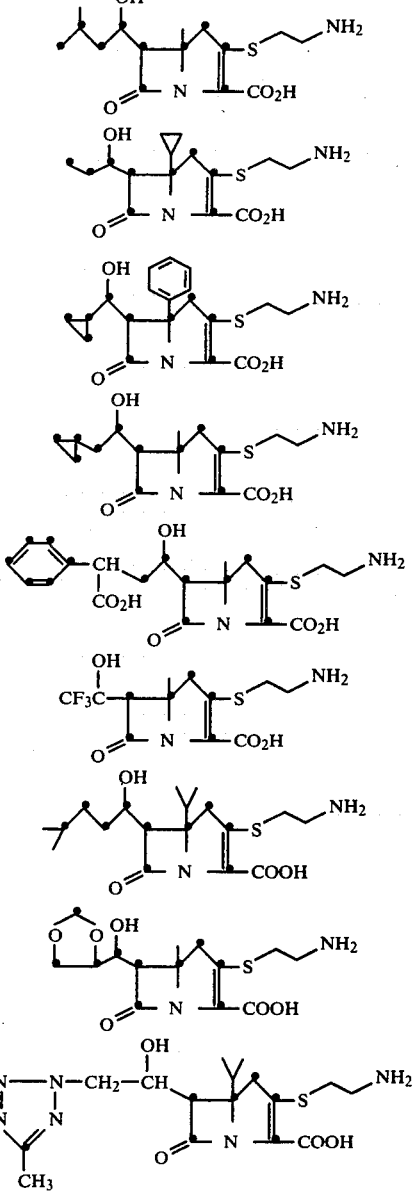

6. A compound according to claim 5 wherein the aminoethylthio side chain,

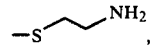

is replaced by a member of the group consisting of:

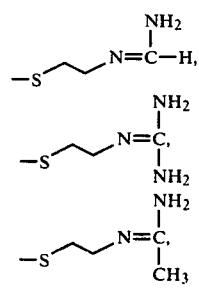

-continued
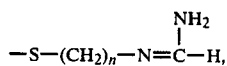
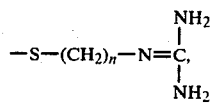
-continued
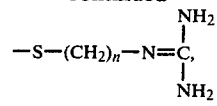
n = 1, 3, 4, 5 or 6.
7. An antibiotic pharmaceutical composition comprising a therapeutically effective amount of a compound according to claim 1 and a pharmaceutical carrier therefor.
* * * * *